US009834594B2

(12) United States Patent
Chang et al.

(10) Patent No.: US 9,834,594 B2

(45) **Date of Patent: *Dec. 5, 2017**

(54) HUMAN MONOCLONAL ANTIBODIES DERIVED FROM HUMAN B CELLS AND HAVING NEUTRALIZING ACTIVITY AGAINST INFLUENZA A VIRUSES

(71) Applicant: CELLTRION, INC., Incheon (KR)

(72) Inventors: Shin Jae Chang, Incheon (KR); Jong Mook Kim, Incheon (KR); Kye Sook Yi, Incheon (KR); Hyun Joo Lee, Incheon (KR)

(73) Assignee: CELLTRION, INC., Incheon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/400,294

(22) Filed: Jan. 6, 2017

(65) Prior Publication Data

US 2017/0158754 A1 Jun. 8, 2017

Related U.S. Application Data

(63) Continuation of application No. 13/583,529, filed on Sep. 7, 2012, now Pat. No. 9,573,991.

(51) Int. Cl.

| | |
|---|---|
| ***A61K 39/395*** | (2006.01) |
| ***C07K 16/10*** | (2006.01) |
| ***G01N 33/569*** | (2006.01) |

(52) U.S. Cl.

CPC ... *C07K 16/1018* (2013.01); *G01N 33/56983* (2013.01); *C07K 2317/21* (2013.01); *C07K 2317/51* (2013.01); *C07K 2317/515* (2013.01); *C07K 2317/76* (2013.01); *C07K 2317/92* (2013.01); *G01N 2333/11* (2013.01); *G01N 2469/10* (2013.01)

(58) Field of Classification Search

None

See application file for complete search history.

(56) References Cited

U.S. PATENT DOCUMENTS 9,573,991 B2 * 2/2017 Chang ................ C07K 16/1018

* cited by examiner

*Primary Examiner* — Shanon A Foley

*Assistant Examiner* — Myron Hill

(74) *Attorney, Agent, or Firm* — Mintz Levin Cohn Ferris Glovsky and Popeo, P.C.; Kongsik Kim; Linyu Mitra

(57) ABSTRACT

The present invention relates to human monoclonal antibodies derived from human B cells present in the blood of patients who had recovered from infection with influenza A viruses, wherein the monoclonal antibodies have neutralizing activity against influenza A viruses. The anti-influenza A virus monoclonal antibody of the present invention has binding and neutralizing activities against at least one influenza A virus selected from the group consisting of influenza A virus H1, H2 and H5 subtypes, and thus it is useful for the prevention and treatment of a disease caused by the influenza A virus and is also useful for diagnosis of influenza A virus infection.

23 Claims, 12 Drawing Sheets

SEQUENCE LISTING

```
<160> NUMBER OF SEQ ID NOS: 45

<210> SEQ ID NO 1
<211> LENGTH: 7
<212> TYPE: PRT
<213> ORGANISM: Artificial Sequence
<220> FEATURE:
<223> OTHER INFORMATION: CT104 antibody light chain CDR1 region

<400> SEQUENCE: 1

Gln Ser Leu Ser Ser Ser Ser
1               5


<210> SEQ ID NO 2
<211> LENGTH: 3
<212> TYPE: PRT
<213> ORGANISM: Artificial Sequence
<220> FEATURE:
<223> OTHER INFORMATION: CT104 antibody light chain CDR2 region

<400> SEQUENCE: 2

Gly Ala Ser
1


<210> SEQ ID NO 3
<211> LENGTH: 9
<212> TYPE: PRT
<213> ORGANISM: Artificial Sequence
<220> FEATURE:
<223> OTHER INFORMATION: CT104 antibody light chain CDR3 region

<400> SEQUENCE: 3

Gln Gln Tyr Gly Asn Ser Pro Tyr Thr
1               5


<210> SEQ ID NO 4
<211> LENGTH: 8
<212> TYPE: PRT
<213> ORGANISM: Artificial Sequence
<220> FEATURE:
<223> OTHER INFORMATION: CT104 antibody heavy chain CDR1 region

<400> SEQUENCE: 4

Gly Gly Thr Leu Asn Asn Tyr Ala
1               5


<210> SEQ ID NO 5
<211> LENGTH: 8
<212> TYPE: PRT
<213> ORGANISM: Artificial Sequence
<220> FEATURE:
<223> OTHER INFORMATION: CT104 antibody heavy chain CDR2 region

<400> SEQUENCE: 5
```

-continued

```
Ile Ser Pro Ile Phe Gly Thr Leu
1               5


<210> SEQ ID NO 6
<211> LENGTH: 13
<212> TYPE: PRT
<213> ORGANISM: Artificial Sequence
<220> FEATURE:
<223> OTHER INFORMATION: CT104 antibody heavy chain CDR3 region

<400> SEQUENCE: 6

Ala Arg Gly Cys Gly Tyr Asn Cys Tyr Tyr Phe Asp Gly
1               5                   10


<210> SEQ ID NO 7
<211> LENGTH: 6
<212> TYPE: PRT
<213> ORGANISM: Artificial Sequence
<220> FEATURE:
<223> OTHER INFORMATION: CT120 antiody light chain CDR1 region

<400> SEQUENCE: 7

Glu Asn Ile Trp Asn Asn
1               5


<210> SEQ ID NO 8
<211> LENGTH: 9
<212> TYPE: PRT
<213> ORGANISM: Artificial Sequence
<220> FEATURE:
<223> OTHER INFORMATION: CT120 antibody light chain CDR3 region

<400> SEQUENCE: 8

Gln Gln Tyr Asn Ser Trp Pro Arg Thr
1               5


<210> SEQ ID NO 9
<211> LENGTH: 8
<212> TYPE: PRT
<213> ORGANISM: Artificial Sequence
<220> FEATURE:
<223> OTHER INFORMATION: CT120 antibody heavy chain CDR1 region

<400> SEQUENCE: 9

Gly Val Phe Phe Ser Ser His Ala
1               5


<210> SEQ ID NO 10
<211> LENGTH: 8
<212> TYPE: PRT
<213> ORGANISM: Artificial Sequence
<220> FEATURE:
<223> OTHER INFORMATION: CT120 antibody heavy chain CDR2 region

<400> SEQUENCE: 10

Ile Ser Pro Met Phe Gly Thr Thr
1               5


<210> SEQ ID NO 11
<211> LENGTH: 16
<212> TYPE: PRT
<213> ORGANISM: Artificial Sequence
<220> FEATURE:
<223> OTHER INFORMATION: CT120 antibody heavy chain CDR3 region

<400> SEQUENCE: 11

Ala Arg Asp Gly Ala Gly Ser Tyr Tyr Pro Leu Asn Trp Phe Asp Pro
```

-continued 1               5                   10                  15

<210> SEQ ID NO 12
<211> LENGTH: 7
<212> TYPE: PRT
<213> ORGANISM: Artificial Sequence
<220> FEATURE:
<223> OTHER INFORMATION: CT123 antibody light chain CDR1 region

<400> SEQUENCE: 12

Gln Ser Val Ser Ile Ser Tyr
1               5

<210> SEQ ID NO 13
<211> LENGTH: 9
<212> TYPE: PRT
<213> ORGANISM: Artificial Sequence
<220> FEATURE:
<223> OTHER INFORMATION: CT123 antibody light chain CDR3 region

<400> SEQUENCE: 13

Gln Gln Tyr Gly Ser Ser Pro Tyr Thr
1               5

<210> SEQ ID NO 14
<211> LENGTH: 8
<212> TYPE: PRT
<213> ORGANISM: Artificial Sequence
<220> FEATURE:
<223> OTHER INFORMATION: CT123 antibody heavy chain CDR1 region

<400> SEQUENCE: 14

Gly Phe Thr Phe Ser Arg Phe Gly
1               5

<210> SEQ ID NO 15
<211> LENGTH: 8
<212> TYPE: PRT
<213> ORGANISM: Artificial Sequence
<220> FEATURE:
<223> OTHER INFORMATION: CT123 antibody heavy chain CDR2 region

<400> SEQUENCE: 15

Ile Trp Tyr Asp Gly Ser Asn Lys
1               5

<210> SEQ ID NO 16
<211> LENGTH: 20
<212> TYPE: PRT
<213> ORGANISM: Artificial Sequence
<220> FEATURE:
<223> OTHER INFORMATION: CT123 antibody heavy chain CDR3 region

<400> SEQUENCE: 16

Ala Lys Asp Ser Arg Gly Tyr Cys Ser Ser Ile Ile Cys Phe Glu Gly
1               5                   10                  15

Gly Leu Asp Asn
            20

<210> SEQ ID NO 17
<211> LENGTH: 21
<212> TYPE: DNA
<213> ORGANISM: Artificial Sequence
<220> FEATURE:
<223> OTHER INFORMATION: CT104 antibody light chain CDR1 region

<400> SEQUENCE: 17
cagagtctta gcagcagctc c 21

<210> SEQ ID NO 18
<211> LENGTH: 9
<212> TYPE: DNA
<213> ORGANISM: Artificial Sequence
<220> FEATURE:
<223> OTHER INFORMATION: CT104 antibody light chain CDR2 region

<400> SEQUENCE: 18 ggtgcatcc 9

<210> SEQ ID NO 19
<211> LENGTH: 27
<212> TYPE: DNA
<213> ORGANISM: Artificial Sequence
<220> FEATURE:
<223> OTHER INFORMATION: CT104 antibody light chain CDR3 region

<400> SEQUENCE: 19
cagcagtatg ggaactcacc gtacacg 27

<210> SEQ ID NO 20
<211> LENGTH: 21
<212> TYPE: DNA
<213> ORGANISM: Artificial Sequence
<220> FEATURE:
<223> OTHER INFORMATION: CT104 antibody heavy chain CDR1 region

<400> SEQUENCE: 20
ggaggcaccc tcaacaacta t 21

<210> SEQ ID NO 21
<211> LENGTH: 24
<212> TYPE: DNA
<213> ORGANISM: Artificial Sequence
<220> FEATURE:
<223> OTHER INFORMATION: CT104 antibody heavy chain CDR2 region

<400> SEQUENCE: 21
atcagcccta tctttgggac atta 24

<210> SEQ ID NO 22
<211> LENGTH: 39
<212> TYPE: DNA
<213> ORGANISM: Artificial Sequence
<220> FEATURE:
<223> OTHER INFORMATION: CT104 antibody heavy chain CDR3 region

<400> SEQUENCE: 22
gcgagaggtt gtggctacaa ttgttactac tttgacggg 39

<210> SEQ ID NO 23
<211> LENGTH: 18
<212> TYPE: DNA
<213> ORGANISM: Artificial Sequence
<220> FEATURE:
<223> OTHER INFORMATION: CT120 antibody light chain CDR1 region

<400> SEQUENCE: 23
gagaatattt ggaacaac 18

<210> SEQ ID NO 24
<211> LENGTH: 27
<212> TYPE: DNA

-continued

```
<213> ORGANISM: Artificial Sequence
<220> FEATURE:
<223> OTHER INFORMATION: CT120 antibody light chain CDR3 region

<400> SEQUENCE: 24

cagcagtata attcgtggcc tcggacg                                          27


<210> SEQ ID NO 25
<211> LENGTH: 24
<212> TYPE: DNA
<213> ORGANISM: Artificial Sequence
<220> FEATURE:
<223> OTHER INFORMATION: CT120 antibody heavy chain CDR1 region

<400> SEQUENCE: 25

ggagtcttct tcagcagtca tgct                                             24


<210> SEQ ID NO 26
<211> LENGTH: 24
<212> TYPE: DNA
<213> ORGANISM: Artificial Sequence
<220> FEATURE:
<223> OTHER INFORMATION: CT120 antibody heavy chain CDR2 region

<400> SEQUENCE: 26

atcagcccta tgtttggaac aaca                                             24


<210> SEQ ID NO 27
<211> LENGTH: 48
<212> TYPE: DNA
<213> ORGANISM: Artificial Sequence
<220> FEATURE:
<223> OTHER INFORMATION: CT120 antibody heavy chain CDR3 region

<400> SEQUENCE: 27

gcgcgtgatg gtgcggggag ttattatcca ctcaactggt tcgacccc                   48


<210> SEQ ID NO 28
<211> LENGTH: 21
<212> TYPE: DNA
<213> ORGANISM: Artificial Sequence
<220> FEATURE:
<223> OTHER INFORMATION: CT123 antibody light chain CDR1 region

<400> SEQUENCE: 28

cagagtgtta gcatcagcta c                                                21


<210> SEQ ID NO 29
<211> LENGTH: 9
<212> TYPE: DNA
<213> ORGANISM: Artificial Sequence
<220> FEATURE:
<223> OTHER INFORMATION: CT123 antibody light chain CDR2 region

<400> SEQUENCE: 29

ggcgcatcc                                                               9


<210> SEQ ID NO 30
<211> LENGTH: 27
<212> TYPE: DNA
<213> ORGANISM: Artificial Sequence
<220> FEATURE:
<223> OTHER INFORMATION: CT123 antibody light chain CDR3 region

<400> SEQUENCE: 30

cagcagtatg gtagctcacc gtacact                                          27
```

-continued

<210> SEQ ID NO 31
<211> LENGTH: 24
<212> TYPE: DNA
<213> ORGANISM: Artificial Sequence
<220> FEATURE:
<223> OTHER INFORMATION: CT123 antibody heavy chain CDR1 region

<400> SEQUENCE: 31
ggattcacct tcagtaggtt tggc 24

<210> SEQ ID NO 32
<211> LENGTH: 24
<212> TYPE: DNA
<213> ORGANISM: Artificial Sequence
<220> FEATURE:
<223> OTHER INFORMATION: CT123 antibody heavy chain CDR2 region

<400> SEQUENCE: 32
atatggtacg atggaagtaa taaa 24

<210> SEQ ID NO 33
<211> LENGTH: 60
<212> TYPE: DNA
<213> ORGANISM: Artificial Sequence
<220> FEATURE:
<223> OTHER INFORMATION: CT123 antibody heavy chain CDR3 region

<400> SEQUENCE: 33
gcgaaagatt cccgcggata ttgtagtagt atcatttgtt ttgagggggg acttgacaac 60

<210> SEQ ID NO 34
<211> LENGTH: 708
<212> TYPE: DNA
<213> ORGANISM: Artificial Sequence
<220> FEATURE:
<223> OTHER INFORMATION: CT104 antibody light chain nucleotide sequence

<400> SEQUENCE: 34
atggaaaccc cagcgcagct tctcttcctc ctgctactct ggctcccaga taccaccgga 60
gaaattgtgt tgacgcagtc tccaggcacc ctgtctttgt ctccagggga aagagccacc 120
ctctcctgca gggccagtca gagtcttagc agcagctcct tagtctggta ccagcagaaa 180
cctggccagg ctcccaggct cctcatctat ggtgcatcca gcagggccac tggcatccca 240
gacaggttca gtggcagtgg gtctgggaca gacttcactc tcaccatcag cagactggag 300
cctgaagatt ttgcagtgta ttactgtcag cagtatggga actcaccgta cacgtttggc 360
caggggaccc aggttgagat caaacgaact gtggctgcac catctgtctt catcttcccg 420
ccatctgatg agcagttgaa atctggaact gcctctgttg tgtgcctgct gaataacttc 480
tatcccagag aggccaaagt acagtggaag gtggataacg ccctccaatc gggtaactcc 540
caggagagtg tcacagagca ggacagcaag gacagcacct acagcctcag cagcaccctg 600
acgctgagca aagcagacta cgagaaacac aaagtctacg cctgcgaagt cacccatcag 660
ggcctgagct cgcccgtcac aaagagcttc aacaggggag agtgttag 708

<210> SEQ ID NO 35
<211> LENGTH: 1410
<212> TYPE: DNA
<213> ORGANISM: Artificial Sequence
<220> FEATURE:
<223> OTHER INFORMATION: CT104 antibody heavy chain nucleotide sequence

<400> SEQUENCE: 35

```
atggactgga cctggaggtt cctctttgtg gtggcagcag ctacaggtgt ccagtcccag     60
gtgcagctgg tgcagtctgg ggctgaggtg aagaagcctg ggtcctcggt gaaggtctcc    120
tgcaaggctt ctggaggcac cctcaacaac tatgctatca gctgggtgcg acaggcccct    180
ggacaagggc ttgagtggat gggagggatc agccctatct ttgggacatt aaactacgca    240
gagaggttcc agggcagagt caccattacc gcggacgtat ttacgaacac agtctacatg    300
gagctgagca gcctgagatc tgaggacacg gccgtgtatt tctgtgcgag aggttgtggc    360
tacaattgtt actactttga cgggtggggc cagggaaccc tggtcaccgt ttcctcagcc    420
tccaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggatgagctg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgagggtc tgcacaacca ctacacgcag   1380
aagagcctct ccctgtctcc gggtaaatga                                    1410
```

<210> SEQ ID NO 36
<211> LENGTH: 235
<212> TYPE: PRT
<213> ORGANISM: Artificial Sequence
<220> FEATURE:
<223> OTHER INFORMATION: CT104 antibody light chain peptide sequence

<400> SEQUENCE: 36

```
Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Leu Ser Ser Ser Ser Leu Val Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
```

-continued

```
            100                 105                 110

Gly Asn Ser Pro Tyr Thr Phe Gly Gln Gly Thr Gln Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235


<210> SEQ ID NO 37
<211> LENGTH: 469
<212> TYPE: PRT
<213> ORGANISM: Artificial Sequence
<220> FEATURE:
<223> OTHER INFORMATION: CT104 antibody heavy chain peptide sequence

<400> SEQUENCE: 37

Met Asp Trp Thr Trp Arg Phe Leu Phe Val Val Ala Ala Ala Thr Gly
1               5                   10                  15

Val Gln Ser Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Leu
        35                  40                  45

Asn Asn Tyr Ala Ile Ser Trp Val Arg Gln Ala Pro Gly Gln Gly Leu
    50                  55                  60

Glu Trp Met Gly Gly Ile Ser Pro Ile Phe Gly Thr Leu Asn Tyr Ala
65                  70                  75                  80

Glu Arg Phe Gln Gly Arg Val Thr Ile Thr Ala Asp Val Phe Thr Asn
                85                  90                  95

Thr Val Tyr Met Glu Leu Ser Ser Leu Arg Ser Glu Asp Thr Ala Val
            100                 105                 110

Tyr Phe Cys Ala Arg Gly Cys Gly Tyr Asn Cys Tyr Tyr Phe Asp Gly
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
```

-continued

```
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Gly Leu His Asn His Tyr Thr Gln Lys Ser Leu Ser
    450                 455                 460

Leu Ser Pro Gly Lys
465
```

<210> SEQ ID NO 38
<211> LENGTH: 705
<212> TYPE: DNA
<213> ORGANISM: Artificial Sequence
<220> FEATURE:
<223> OTHER INFORMATION: CT120 antibody light chain nucleotide sequence

<400> SEQUENCE: 38

```
atggaagccc cagctcagct tctcttcctc ctgctactct ggctcccaga taccaccgga     60

gaaattgtgt tgacacagtc tccagccacc ttgtctttgt ctccagggga aagagccacc    120

ctctcctgca gggccagtga gaatatttgg aacaacttgg cctggtacca gcaaaaacct    180

ggccaggctc ccaggctcct catctctggt gcgtccaccg gggccactgg tgtcccaagt    240

aggtttagag gcagcgggtc taggacagaa ttcactctca ccatcagcag cctgcagtct    300

gaagattttg caatttattt ctgtcagcag tataattcgt ggcctcggac gttcggccca    360

gggaccaagg tggagatcaa acgaactgtg gctgcaccat ctgtcttcat cttcccgcca    420

tctgatgagc agttgaaatc tggaactgcc tctgttgtgt gcctgctgaa taacttctat    480

cccagagagg ccaaagtaca gtggaaggtg gataacgccc tccaatcggg taactcccag    540

gagagtgtca cagagcagga cagcaaggac agcacctaca gcctcagcag caccctgacg    600

ctgagcaaag cagactacga gaaacacaaa gtctacgcct gcgaagtcac ccatcagggc    660
```

-continued ctgagctcgc ccgtcacaaa gagcttcaac aggggagagt gttag 705

<210> SEQ ID NO 39
<211> LENGTH: 1419
<212> TYPE: DNA
<213> ORGANISM: Artificial Sequence
<220> FEATURE:
<223> OTHER INFORMATION: CT120 antibody heavy chain nucleotide sequence

<400> SEQUENCE: 39
atggactgga cctggaggtt cctctttgtg gtggcagcag ctacaggtgt ccagtgccag 60
gtgcagctgg tgcagtctgg ggctgaggtg aagatgcctg ggtcctcggt gaaggtctcc 120
tgcaagactt ctggagtctt cttcagcagt catgctatca gttgggtgcg acaggcccct 180
ggacaagggc ttgagtggat gggagggatc agccctatgt ttggaacaac acactacgca 240
cagaagttcc agggcagagt cacgattacc gcggaccaat ccacgaccac agcctacatg 300
gagttgacca gtcttacatc tgaggacacg gccgtatatt actgtgcgcg tgatggtgcg 360
gggagttatt atccactcaa ctggttcgac ccctggggcc agggaaccct ggtcaccgtc 420
tcctcagcct ccaccaaggg cccatcggtc ttccccctgg caccctcctc caagagcacc 480
tctgggggca cagcggccct gggctgcctg gtcaaggact acttccccga accggtgacg 540
gtgtcgtgga actcaggcgc cctgaccagc ggcgtgcaca ccttcccggc tgtcctacag 600
tcctcaggac tctactccct cagcagcgtg gtgaccgtgc cctccagcag cttgggcacc 660
cagacctaca tctgcaacgt gaatcacaag cccagcaaca ccaaggtgga caagagagtt 720
gagcccaaat cttgtgacaa aactcacaca tgcccaccgt gcccagcacc tgaactcctg 780
gggggaccgt cagtcttcct cttcccccca aaacccaagg acaccctcat gatctcccgg 840
acccctgagg tcacatgcgt ggtggtggac gtgagccacg aagaccctga ggtcaagttc 900
aactggtacg tggacggcgt ggaggtgcat aatgccaaga caaagccgcg ggaggagcag 960
tacaacagca cgtaccgtgt ggtcagcgtc ctcaccgtcc tgcaccagga ctggctgaat 1020
ggcaaggagt acaagtgcaa ggtctccaac aaagccctcc cagcccccat cgagaaaacc 1080
atctccaaag ccaaagggca gccccgagaa ccacaggtgt acaccctgcc cccatcccgg 1140
gatgagctga ccaagaacca ggtcagcctg acctgcctgg tcaaaggctt ctatcccagc 1200
gacatcgccg tggagtggga gagcaatggg cagccggaga acaactacaa gaccacgcct 1260
cccgtgctgg actccgacgg ctccttcttc ctctacagca agctcaccgt ggacaagagc 1320
aggtggcagc aggggaacgt cttctcatgc tccgtgatgc atgagggtct gcacaaccac 1380
tacacgcaga agagcctctc cctgtctccg ggtaaatga 1419

<210> SEQ ID NO 40
<211> LENGTH: 234
<212> TYPE: PRT
<213> ORGANISM: Artificial Sequence
<220> FEATURE:
<223> OTHER INFORMATION: CT120 antibody light chain peptide sequence

<400> SEQUENCE: 40

Met Glu Ala Pro Ala Gln Leu Leu Phe Leu Leu Leu Leu Trp Leu Pro
1 5 10 15

Asp Thr Thr Gly Glu Ile Val Leu Thr Gln Ser Pro Ala Thr Leu Ser
20 25 30

Leu Ser Pro Gly Glu Arg Ala Thr Leu Ser Cys Arg Ala Ser Glu Asn
35 40 45

```
Ile Trp Asn Asn Leu Ala Trp Tyr Gln Gln Lys Pro Gly Gln Ala Pro
    50                  55                  60

Arg Leu Leu Ile Ser Gly Ala Ser Thr Gly Ala Thr Gly Val Pro Ser
65                  70                  75                  80

Arg Phe Arg Gly Ser Gly Ser Arg Thr Glu Phe Thr Leu Thr Ile Ser
                85                  90                  95

Ser Leu Gln Ser Glu Asp Phe Ala Ile Tyr Phe Cys Gln Gln Tyr Asn
            100                 105                 110

Ser Trp Pro Arg Thr Phe Gly Pro Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 41
<211> LENGTH: 472
<212> TYPE: PRT
<213> ORGANISM: Artificial Sequence
<220> FEATURE:
<223> OTHER INFORMATION: CT120 antibody heavy chain peptide sequence

<400> SEQUENCE: 41

Met Asp Trp Thr Trp Arg Phe Leu Phe Val Val Ala Ala Ala Thr Gly
1               5                   10                  15

Val Gln Cys Gln Val Gln Leu Val Gln Ser Gly Ala Glu Val Lys Met
            20                  25                  30

Pro Gly Ser Ser Val Lys Val Ser Cys Lys Thr Ser Gly Val Phe Phe
        35                  40                  45

Ser Ser His Ala Ile Ser Trp Val Arg Gln Ala Pro Gly Gln Gly Leu
    50                  55                  60

Glu Trp Met Gly Gly Ile Ser Pro Met Phe Gly Thr Thr His Tyr Ala
65                  70                  75                  80

Gln Lys Phe Gln Gly Arg Val Thr Ile Thr Ala Asp Gln Ser Thr Thr
                85                  90                  95

Thr Ala Tyr Met Glu Leu Thr Ser Leu Thr Ser Glu Asp Thr Ala Val
            100                 105                 110

Tyr Tyr Cys Ala Arg Asp Gly Ala Gly Ser Tyr Tyr Pro Leu Asn Trp
        115                 120                 125

Phe Asp Pro Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175
```

-continued

```
Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Gly Leu His Asn His Tyr Thr Gln Lys
    450                 455                 460

Ser Leu Ser Leu Ser Pro Gly Lys
465                 470
```

<210> SEQ ID NO 42
<211> LENGTH: 708
<212> TYPE: DNA
<213> ORGANISM: Artificial Sequence
<220> FEATURE:
<223> OTHER INFORMATION: CT123 antibody light chain nucleotide sequence

<400> SEQUENCE: 42

```
atggaaaccc cagcgcagct tctcttcctc ctgctactct ggctcccaga taccaccgga     60

gaaactgtgt tgacgcagtc tccaggcacc ctgtctttgt ctccagggga aagagccacc    120

ctctcctgca gggccagtca gagtgttagc atcagctact tagcctggta ccagcggaaa    180

cctggccagg ctcccaggct cctcatctat ggcgcatcca ggagggccac tggcatccca    240

gacaggttca gtggcagtgg gtctgggaca gacttcactc tcaccatcag cagactggag    300

cctgaagatt ttgcagtata ttactgtcag cagtatggta gctcaccgta cacttttggc    360
```

-continued

```
caggggacca agctggagat caaacgaact gtggctgcac catctgtctt catcttcccg    420

ccatctgatg agcagttgaa atctggaact gcctctgttg tgtgcctgct gaataacttc    480

tatcccagag aggccaaagt acagtggaag gtggataacg ccctccaatc gggtaactcc    540

caggagagtg tcacagagca ggacagcaag gacagcacct acagcctcag cagcaccctg    600

acgctgagca aagcagacta cgagaaacac aaagtctacg cctgcgaagt cacccatcag    660

ggcctgagct cgcccgtcac aaagagcttc aacaggggag agtgttag                 708
```

<210> SEQ ID NO 43
<211> LENGTH: 1431
<212> TYPE: DNA
<213> ORGANISM: Artificial Sequence
<220> FEATURE:
<223> OTHER INFORMATION: CT123 antibody heavy chain nucleotide sequence

<400> SEQUENCE: 43

```
atggagtttg ggctgagctg ggttttcctc gttgctcttt taagaggtgt ccagtgtcag     60

gtgcagctgg tggagtctgg gggaggcgtg gtccagcctg ggaggtccct gagactctcc    120

tgtgcagcgt ctggattcac cttcagtagg tttggcatcc actgggtccg ccaggctcca    180

ggcaaggggc tggagtggat ggcagttata tggtacgatg gaagtaataa attctatgca    240

gactccgtga agggccgatt caccatctcc agagacaatt ccaagaacac ggtttatctg    300

caaatgaaca gcctcagagc cgaggacacg gctgtctatt actgtgcgaa agattcccgc    360

ggatattgta gtagtatcat ttgttttgag gggggacttg acaactgggg ccagggaacc    420

ctggtcaccg tctcctcagc ctccaccaag ggcccatcgg tcttccccct ggcaccctcc    480

tccaagagca cctctggggg cacagcggcc ctgggctgcc tggtcaagga ctacttcccc    540

gaaccggtga cggtgtcgtg gaactcaggc gccctgacca gcggcgtgca caccttcccg    600

gctgtcctac agtcctcagg actctactcc ctcagcagcg tggtgaccgt gccctccagc    660

agcttgggca cccagaccta catctgcaac gtgaatcaca agcccagcaa caccaaggtg    720

gacaagagag ttgagcccaa atcttgtgac aaaactcaca catgcccacc gtgcccagca    780

cctgaactcc tggggggacc gtcagtcttc ctcttccccc caaaacccaa ggacaccctc    840

atgatctccc ggacccctga ggtcacatgc gtggtggtgg acgtgagcca cgaagaccct    900

gaggtcaagt tcaactggta cgtggacggc gtggaggtgc ataatgccaa gacaaagccg    960

cgggaggagc agtacaacag cacgtaccgt gtggtcagcg tcctcaccgt cctgcaccag   1020

gactggctga atggcaagga gtacaagtgc aaggtctcca acaaagccct cccagccccc   1080

atcgagaaaa ccatctccaa agccaaaggg cagccccgag aaccacaggt gtacaccctg   1140

cccccatccc gggatgagct gaccaagaac caggtcagcc tgacctgcct ggtcaaaggc   1200

ttctatccca gcgacatcgc cgtggagtgg gagagcaatg ggcagccgga gaacaactac   1260

aagaccacgc ctcccgtgct ggactccgac ggctccttct tcctctacag caagctcacc   1320

gtggacaaga gcaggtggca gcaggggaac gtcttctcat gctccgtgat gcatgagggt   1380

ctgcacaacc actacacgca gaagagcctc tccctgtctc cgggtaaatg a            1431
```

<210> SEQ ID NO 44
<211> LENGTH: 235
<212> TYPE: PRT
<213> ORGANISM: Artificial Sequence
<220> FEATURE:
<223> OTHER INFORMATION: CT123 antibody light chain peptide sequence

<400> SEQUENCE: 44

```
Met Glu Thr Pro Ala Gln Leu Leu Phe Leu Leu Leu Leu Trp Leu Pro
1               5                   10                  15

Asp Thr Thr Gly Glu Thr Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ile Ser Tyr Leu Ala Trp Tyr Gln Arg Lys Pro Gly Gln Ala
    50                  55                  60

Pro Arg Leu Leu Ile Tyr Gly Ala Ser Arg Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Tyr Thr Phe Gly Gln Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235


<210> SEQ ID NO 45
<211> LENGTH: 476
<212> TYPE: PRT
<213> ORGANISM: Artificial Sequence
<220> FEATURE:
<223> OTHER INFORMATION: CT123 antibody heavy chain peptide sequence

<400> SEQUENCE: 45

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Arg Phe Gly Ile His Trp Val Arg Gln Ala Pro Gly Lys Gly Leu
    50                  55                  60

Glu Trp Met Ala Val Ile Trp Tyr Asp Gly Ser Asn Lys Phe Tyr Ala
65                  70                  75                  80

Asp Ser Val Lys Gly Arg Phe Thr Ile Ser Arg Asp Asn Ser Lys Asn
                85                  90                  95

Thr Val Tyr Leu Gln Met Asn Ser Leu Arg Ala Glu Asp Thr Ala Val
            100                 105                 110

Tyr Tyr Cys Ala Lys Asp Ser Arg Gly Tyr Cys Ser Ser Ile Ile Cys
        115                 120                 125
```

-continued

```
Phe Glu Gly Gly Leu Asp Asn Trp Gly Gln Gly Thr Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Arg Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Gly Leu His Asn His
    450                 455                 460

Tyr Thr Gln Lys Ser Leu Ser Leu Ser Pro Gly Lys
465                 470                 475
```

HUMAN MONOCLONAL ANTIBODIES DERIVED FROM HUMAN B CELLS AND HAVING NEUTRALIZING ACTIVITY AGAINST INFLUENZA A VIRUSES

CROSS-REFERENCES TO RELATED APPLICATIONS

This application is a continuation application of U.S. application Ser. No. 13/583,529, filed on Sep. 7, 2012, which is a U.S. national phase application, pursuant to 35 U.S.C. §371, of PCT/KR2011/001563, filed Mar. 7, 2011, designating the United States, which claims priority to Korean Application No. 10-2010-0020587, filed Mar. 8, 2010. The entire contents of the aforementioned patent applications are incorporated herein by reference.

INCORPORATION BY REFERENCE OF SEQUENCE LISTING

The contents of the text file named 48169-569C01US_ST25.TXT, which was created on Feb. 2, 2017, and is 35,635 bytes in size, are hereby incorporated by reference in their entireties.

TECHNICAL FIELD

The present invention relates to human monoclonal antibodies derived from human B cells present in the blood of patients who had recovered from infection with influenza A viruses, wherein the monoclonal antibodies have neutralizing activity against influenza A viruses.

BACKGROUND ART

Influenza, an illness caused by respiratory infection with influenza viruses, often occurs in winter. It is known to have very high infectivity and to affect all age groups, particularly elderly people (Treanor J, 2004, *N Etzgl J Med.* 350(3):218-20). Influenza virus is a negative-stranded and enveloped RNA (ribonucleic acid) virus belonging to the family Orthomyxoviridae. This family has eight segments of single-stranded RNA and are classified as influenza types A, B and C. Influenza A viruses are further divided into subtypes on the basis of their major surface proteins hemagglutinin (HA) and neuraminidase (NA). Up to date, 16 HAs and 9 NAs have been identified (Cheung T K and Poon L L 2007, *Ann NY Acad Sci.* 1102:1-25). Influenza viruses infect a wide range of animals including birds, pigs and humans depending on their types and have a genome composed of segmented RNAs. For this reason, influenza viruses can continuously mutate and recombine, resulting in new genetic variations (Treanor J, 2004. *N Engl J Med.* 350(3): 218-20). For this reason, it is difficult to obtain permanent immunity against influenza viruses. The most effective prevention method currently used is vaccination against particular influenza viruses expected to be prevalent.

Influenza Vaccines are generally produced using eggs, but this is an inefficient method that requires much time. Accordingly, this method has a problem in that it is difficult to produce sufficient amounts of vaccines each year within a limited time frame. To solve this problem, studies on methods of producing vaccines by cell culture are being actively conducted in several pharmaceutical companies (GSK, Baxter, etc.). In addition, it is very difficult to develop a vaccine rapidly against the pandemic influenza virus when pandemic infection occurs. Also, antiviral drugs are not completely reliable due to a problem associated with the appearance of mutant viruses having resistance.

To solve this problem, recently antibodies against influenza viruses have been actively developed for a therapeutic purpose (Throsby et al, 2008, *PloS One* 3 (e3942); Sui et al., 2009, *Nature structural & molecular biology.* 16 (265-273); Simmons et al, 2007, *PloS Medicine* 4 (e178)).

Blood products from recovered patients have been used to treat patients infected with various viruses, as well as to treat pandemic flu infections. For example, when patients infected with Spanish influenza virus had symptoms of pneumonia, blood products collected from patients who recovered from infection with the flu are used to treat the flu (Luke et al., 2006. *Annals of internal medicine.* 145:599). As such, hyperimmune globulin (IgIv) is purified from human plasma and used to treat patients infected with various viruses, but the product obtained as described above may not be safe from potential infectious agents in blood and is inefficient for mass production.

Human B cells are used for the screening of specific human monoclonal antibodies. However, immortalization of human B cells by Epstein-Barr virus (EBV) is inefficient in immortalization of B-cells and is time-consuming. To overcome this inefficiency, new techniques are being developed and used. One of these techniques is to use an RTPCR method to obtain genetic information for an antibody directly from B cells. For example, there is a method comprising staining B cells that express an antibody to a specific antigen, isolating the B cells using a FACS sorter, obtaining genetic information for the antibody from the single B cells by an RT-PCR method, inserting the genetic information into an expression vector, and transfecting the expression vector into animal cells, thereby producing a large amount of the antibody. To perform such a production in an easier and rapid manner, the following technique can be used. The new technique "immunospot array assay on a chip" (ISAAC) enables an antibody gene to be obtained by screening single B cells, which secrete a specific monoclonal antibody, within several weeks (Jin et al., 2009 *Nat Med.* 15, 1088-1092). The antibody thus obtained is a natural human antibody which can be more effective in terms of immunogenic issues.

SUMMARY

It is an object of the present invention to provide a human monoclonal antibody, which is derived from human B cells and has neutralizing activity against influenza A virus.

Another object of the present invention is to provide an isolated nucleic acid molecule encoding said monoclonal antibody.

Still another object of the present invention is to provide an expression vector containing said nucleic acid molecule inserted therein.

Still another object of the present invention is to provide an antibody-producing cell line transfected with said expression vector.

Still another object of the present invention is to provide a method for screening a human monoclonal antibody.

Still another object of the present invention is to provide a composition comprising said human monoclonal antibody.

Still another object of the present invention is to provide a method of treating a disease caused by influenza A virus using said human monoclonal antibody.

Still another object of the present invention is to provide a method of preventing a disease caused by influenza A virus using said human monoclonal antibody.

Still another object of the present invention is to provide a method for diagnosis of influenza A virus infection using said human monoclonal antibody.

Yet another object of the present invention is to provide a kit for diagnosis of influenza A virus, which comprises said human monoclonal antibody.

To achieve the abovegoals, the present invention provides an anti-influenza A virus monoclonal antibody having neutralizing activity against at least one influenza A virus selected from the group consisting of influenza A virus H1, H2 and H5 subtypes.

The present invention also provides an isolated nucleic acid molecule encoding said monoclonal antibody.

The present invention also provides an expression vector containing said isolated nucleic acid molecule inserted therein.

The present invention also provides an antibody-producing cell line transfected with said expression vector.

The present invention also provides a method for screening a human monoclonal antibody.

The present invention also provides a composition comprising said human monoclonal antibody.

The present invention also provides a composition for preventing and treating a disease caused by influenza A virus, the composition comprising said human monoclonal antibody.

The present invention also provides a composition for diagnosis of influenza A virus infection, the composition comprising said human monoclonal antibody.

The present invention also provides a method of treating a disease caused by influenza A virus using said human monoclonal antibody.

The present invention also provides a method of preventing a disease caused by influenza A virus using said human monoclonal antibody.

The present invention also provides a method for diagnosis of influenza A virus infection using said human monoclonal antibody.

The present invention also provides a kit for diagnosis of influenza A virus, which comprises said human monoclonal antibody.

The anti-influenza A virus monoclonal antibody of the present invention has binding and neutralizing activities against at least one influenza A virus selected from the group consisting of influenza A virus H1, H2 and H5 subtypes, and thus it is useful for the prevention and treatment of a disease caused by the influenza A virus and is also useful for diagnosis of influenza A virus infection.

DETAILED DESCRIPTION

Figure 1:
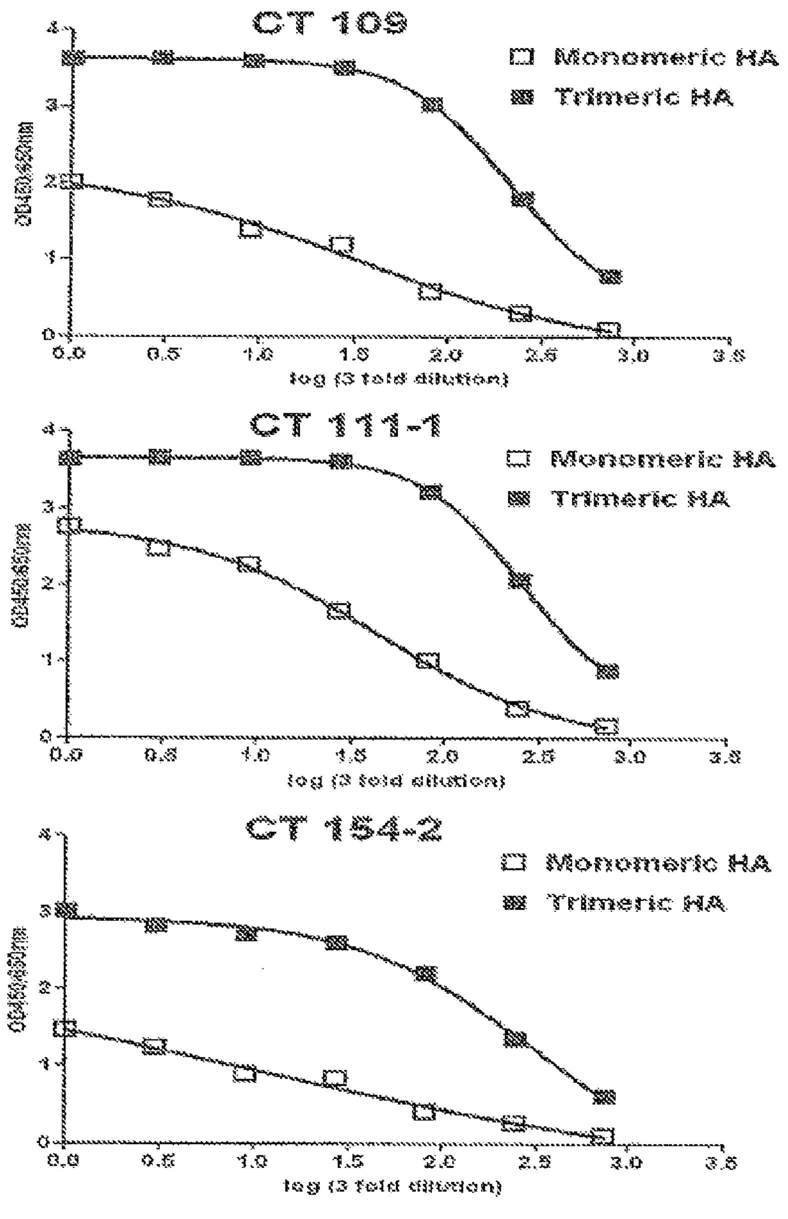
FIG. 1 is a set of graphs showing the binding affinities of CT109, CT111-1 and CT14-2 antibodies to monomeric Hemagglutinin (hereinafter referred to as "HA") and trimeric HA.

Hereinafter, terms used herein will be defined as follows.

The term "influenza A viruses" refers to negative-strand and enveloped RNA(ribonucleic acid) virus belonging to the family Orthomyxoviridae. They have eight segments of single-stranded RNA and are classified as influenza types A, B and C. They are further divided into subtypes on the basis of their major surface proteins HA (hemagglutinin) and NA (neuraminidase). Prior to the invention described herein, 16 Has and 9 NAs were known.

The term "Hl subtype" used herein is intended to include H1N1, H1N2, H1N3, H1N4, H1N5, H1N6, H1N7, H1N8 and H1N9 of influenza A virus.

The term "H2 subtype" used herein is intended to include H2N1, H2N2, H2N3, H2N4, H2N5, H2N6, H2N7, H2N8 and H2N9 of influenza A virus.

The term "H5 subtype" used herein is intended to include H5N1, H5N2, H5N3, H5N4, H5N5, H5N6, H5N7, H5N8 and H5N9 of influenza A virus.

The term "hemagglutinin" (hereinafter referred to as "HA") indicates the envelope glycoprotein of influenza virus. HA mediates the adsorption and penetration of influenza virus into a host cell. There are 16 known HA subtypes.

The term "recovered or completely recovered patients" used herein refers to patients who were positive for influenza A virus due to influenza A virus infection, but are negative for influenza A virus in blood after a given period of time, indicating that the patients had recovered from infection with influenza A virus.

Hereinafter, the present invention will be described in detail.

The present inventors isolated peripheral blood mononuclear cells (PBMCs) from blood collected from patients who had recovered from infection with influenza A virus. Monoclonal antibody-producing B cells were screened from the isolated PBMCs. The genetic information for producing monoclonal antibodies in the screened B cells was obtained by an RT-PCR method and inserted into a pcDNA vector. The vector was transfected into a CHO cell line to confirm preliminary antibody production and it's HA-binding activity. A total of 82 antibodies were screened. To more accurately measure binding affinity to HA, all the antibodies inserted into the pcDNA vector were transfected into human F2N cells, and antibodies generated from the transfected cells were comparatively analyzed by HA-ELISA using monomeric HA and trimeric HA as antigens, thereby 35 antibodies were selected, which were reacted with the trimeric HA at higher degree than with the monomeric HA. The 35 selected antibody genes in the pcDNA vectors were inserted into MarEx expression vectors, and then transfected into F2N cells to produce a larger amount of antibodies. These antibodies were used for a microneutralization test (hereinafter referred to as an "MN test") and a hemagglutination inhibition test (hereinafter referred to as an "HI test") to determine the neutralizing activities against various influenza viruses. A number of the antibodies exhibited high or low neutralizing activities against various influenza viruses, but all the antibodies showed a negative reaction in the HI test. Through the MN test, three monoclonal antibodies (CT104, CT120 and CT123 antibodies) showing neutralizing activity against various viruses were finally selected. It was found that, among the three screened monoclonal antibodies, the CT104 had neutralizing activity against the H1 and H5 subtypes, the CT120 had neutralizing activity against the H1, H2 and H5 subtypes, and the CT123 had neutralizing activity against the H1 subtype (see Table 1). Also, in animal (mouse) survival experiments conducted using the H1 and H5 subtype, the CT104 and the C120 exhibited excellent preventive and therapeutic effects against H5N1 infection, and the three antibodies all exhibited excellent preventive effects against pandemic and seasonal H1N1 infections (see FIG. 6). In another animal (ferret) experiments conducted using the H1 subtype, the CT120 exhibited therapeutic effects against H1N1 (A/California/04/09) infection (see FIG. 7 and FIG. 8). Based on the above results, the present inventors have completed an invention of neutralizing monoclonal antibodies which protect against influenza A virus infection.

Accordingly, the present invention provides an monoclonal antibody having neutralizing activity against influenza A virus H1, H2 and H5 subtypes.

In the present invention, the monoclonal antibody preferably binds to HA on the surface of influenza A virus. Also, the monoclonal antibody is preferably derived from B cells present in the blood of patients who had recovered from infection with the influenza A virus H1N1 subtype.

In the present invention, the influenza A virus is preferably of the H1N1 subtype, and the influenza A virus HINI subtype is at least one influenza virus selected from the group consisting of A/Texas/05/2009-RG15, A/New York/18/2009-RG15, A/Solomon Islands/2006 and A/Ohio/83. Also, the influenza A virus is preferably of the H2N2 subtype, and the influenza A virus H2N2 subtype is A/Ann Arbor/6/60 ca. In addition, the influenza A virus is preferably of the H5N1 subtype, and the influenza A virus H5N1 subtype is one influenza virus selected among A/Vietnam/1203/04 and A/Anhui/1/05.

In the present invention, the monoclonal antibody has no neutralizing activity against the influenza A virus H3N2 subtype.

The present invention also provides an anti-influenza A virus monoclonal antibody comprising the following light-chain and heavy-chain polypeptide sequences, and a fragment and functional variant thereof:

a light chain comprising a CDR1 region comprising sequence(s) selected from the group consisting of SEQ ID NO: 1, SEQ ID NO: 7 and SEQ ID NO: 12, a CDR2 region comprising a sequence of of SEQ ID NO: 2, and a CDR3 region comprising sequence(s) selected from the group consisting of SEQ ID NO: 3, SEQ ID NO: 8 and SEQ ID NO: 13; and a heavy chain comprising a CDR1 region comprising sequence(s) selected from the group consisting of SEQ ID NO: 4, SEQ ID NO: 9 and SEQ ID NO: 14, a CDR2 region comprising sequence(s) selected from the group consisting of SEQ ID NO: 5, SEQ ID NO: 10 and SEQ ID NO: 15, and a CDR3 region comprising sequence(s) selected from the group consisting of SEQ ID NO: 6, SEQ ID NO: 11 and SEQ ID NO: 16.

The present invention also provides an anti-influenza A virus monoclonal antibody selected from the group consisting of the following monoclonal antibodies, and a fragment and functional variant thereof:

a monoclonal antibody comprising a light chain comprising a CDR1 region comprising a sequence of SEQ ID NO: 1, a CDR2 region comprising a sequence of SEQ ID NO: 2 and a CDR3 region comprising a sequence of SEQ ID NO: 3, and a heavy chain comprising a CDR1 region comprising a sequence of SEQ ID NO: 4, a CDR2 region comprising a sequence of SEQ ID NO: 5, and a CDR3 region comprising a sequence of SEQ ID NO: 6;

a monoclonal antibody comprising a light chain comprising a CDR1 region comprising a sequence of SEQ ID NO: 7, a CDR2 region comprising a sequence of SEQ ID NO: 2 and a CDR3 region comprising a sequence of SET ID NO: 8, and a heavy chain comprising a CDR1 region comprising a sequence of SEQ ID NO: 9, a CDR2 region comprising a sequence of SEQ ID NO: 10 and a CDR3 region comprising a sequence of SEQ ID NO: 11; and a monoclonal antibody comprising a light chain comprising a CDR1 region comprising a sequence of SEQ ID NO: 12, a CDR2 region comprising a sequence of SEQ ID NO: 2 and a CDR3 region comprising a sequence of SEQ ID NO: 13, and a heavy chain comprising a CDR1 region comprising a sequence of SEQ ID NO: 14, a CDR2 region comprising a sequence of SEQ ID NO: 15 and a CDR3 region comprising a sequence of SEQ ID NO: 16.

The monoclonal antibody preferably comprises a light chain comprising a polypeptide sequence of SEQ ID NO: 36, and a heavy chain comprising a polypeptide sequence of SEQ ID NO: 37. The monoclonal antibody preferably has neutralizing activity against the influenza A virus H1 and H5 subtypes and has no neutralizing activity against the influenza A virus H3 subtype. The H1 subtype includes H1N1, H1N2, H1N3, H1N4, H1N5, H1N6, H1N7, H1N8 and H1N9, and the H5 subtype includes H5N1, H5N2, H5N3, H5N4, H5N5, H5N6, H5N7, H5N8 and H5N9.

The monoclonal antibody preferably comprises a light chain comprising a polypeptide sequence of SEQ ID NO: 40, and a heavy chain comprising a polypeptide sequence of SEQ ID NO: 41. The monoclonal antibody preferably has neutralizing activity against the influenza A virus H1, H2 and H5 subtypes and has no neutralizing activity against the influenza A virus H3 subtype. The H1 subtype includes H1N1, H1N2, H1N3, H1N4, H1N5, H1N6, H1N7, H1N8 and H1N9, and the H2 subtype includes H2N1, H2N2, H2N3, H2N4, H2N5, H2N6, H2N7, H2N8 and H2N9. Also, the H5 subtype includes H5N1, H5N2, H5N3, H5N4, H5N5, H5N6, H5N7, H5N8 and H5N9.

The monoclonal antibody preferably comprises a light chain comprising a polypeptide sequence of SEQ ID NO: 44, and a heavy chain comprising a polypeptide sequence of SEQ ID NO: 45. The monoclonal antibody preferably has neutralizing activity against the influenza A virus H1 subtype and has no neutralizing activity against the influenza A virus H3 subtype. The H1 subtype includes H1N1, H1N2, H1N3, H1N4, H1N5, H1N6, H1N7, H1N8 and H1N9.

A fragment of the influenza A virus monoclonal antibody is not the whole antibody, but is a portion of the antibody. It has the ability to bind to the influenza A virus HA, and is meant to include all the fragments which bind to the HA competitively with the anti-influenza A virus monoclonal antibody of the present invention.

In addition, also included are functional variants of the monoclonal antibody. If variants of the monoclonal antibody can complete with the monoclonal antibody of the present invention for binding specifically to the influenza A virus HI, H2 and H5 subtypes, and fragments thereof, they are regarded as functional variants of the monoclonal antibody. Specifically, if functional variants can bind to the influenza A virus H1, H2 and H5 subtypes, or fragments thereof, and have neutralizing activity against such subtypes or fragments, they are regarded as the functional variants. Functional variants include, but are not limited to, derivatives that are substantially similar in primary structural sequence, but which contain e.g. in vitro or in vivo modifications, chemical and/or biochemical, that are not found in the parent monoclonal antibody of the present invention. Such modifications include, for example, acetylation, acylation, covalent attachment of a nucleotide or nucleotide derivative, covalent attachment of a lipid or lipid derivative, cross-linking, disulfide bond formation, glycosylation, hydroxylation, methylation, oxidation, pegylation, proteolytic processing, phosphorylation, and the like. Alternatively, functional variants can be monoclonal antibodies comprising an amino acid sequence containing substitutions, insertions, deletions or combinations thereof of one or more amino acids compared to the amino acid sequences of the parental monoclonal antibodies. Furthermore, functional variants can comprise truncations of the amino acid sequence at either or both of the amino or carboxyl termini. Functional variants according to the present invention may have the same or different, either higher or lower, binding affinities compared to the parental monoclonal antibody but are still capable of binding to the influenza A virus H1, H2 and H5 subtypes, or fragments thereof. For example, functional variants according to the invention may have increased or decreased binding affinities for the influenza A virus H1, H2 and H5 subtypes, or fragments thereof, compared to the parental binding molecules. Preferably, the amino acid sequences of the variable regions, including, but not limited to, framework regions, hypervariable regions, in particular the CDR3 regions, are modified. Generally, the light-chain or heavy chain regions comprise three hypervariable regions, comprising three CDRs, and more conserved regions, the so-called framework regions (FRs). The hypervariable regions comprise amino acid residues from CDRs and amino acid residues from hypervariable loops. Functional variants intended to fall within the scope of the present invention have at least about 50-99%, preferably at least about 60-99%, more preferably at least about 80-99%, even more preferably at least about 90-99%, in particular at least about 95-99%, and in particular at least about 97-99% amino acid sequence homology with the parental monoclonal antibody as defined herein. Computer algorithms such as Gap or Bestfit known to a person skilled in the art can be used to optimally align amino acid sequences to be compared and to define similar or identical amino acid residues. Functional variants can be obtained either by altering the parental monoclonal antibodies or parts thereof by general molecular biology methods known in the art including PCR, oligonucleotide-directed mutagenesis and site-directed mutagenesis, or by organic synthetic methods.

The present invention also provides an anti-influenza A virus monoclonal antibody comprising the following light-chain and heavy-chain polynucleotide sequences, and a fragment and functional variant thereof:

a light chain comprising a CDR1 region comprising sequence(s) selected from the group consisting of SEQ ID NO: 17, SEQ ID NO: 23 and SEQ ID NO: 28, a CDR2 region comprising a sequence of SEQ ID NO: 18 or SEQ ID NO: 29, and a CDR3 region comprising sequence(s) selected from the group consisting of SEQ ID NO: 19, SEQ ID NO: 24 and SEQ ID NO: 30; and a heavy chain comprising a CDR1 region comprising sequence(s) selected from the group consisting of SEQ ID NO: 20, SEQ ID NO: 25 and SEQ ID NO: 31, a CDR2 region comprising sequence(s) selected from the group consisting of SEQ ID NO: 21, SEQ ID NO: 26 and SEQ ID NO: 32, and a CDR3 region comprising sequence(s) selected from the group consisting of SEQ ID NO: 22, SEQ ID NO: 27 and SEQ ID NO: 33.

The present invention also provides an anti-influenza A virus monoclonal antibody selected from the group consisting of the following monoclonal antibodies, and a fragment and functional variant thereof:

a monoclonal antibody comprising a light chain comprising a CDR1 region comprising a sequence of SEQ ID NO: 17, a CDR2 region comprising a sequence of SEQ ID NO: 18 and a CDR3 region comprising a sequence of SEQ ID NO: 19, and a heavy chain comprising a CDR1 region comprising a sequence of SEQ ID NO: 20, a CDR2 region comprising a sequence of SEQ ID NO: 21 and a CDR3 region comprising a sequence of SEQ ID NO: 22;

a monoclonal antibody comprising a light chain comprising a CDR1 region comprising a sequence of SEQ ID NO: 23, a CDR2 region comprising a sequence of SEQ ID NO: 18 and a CDR3 region comprising a sequence of SEQ ID NO: 24, and a heavy chain comprising a CDR1 region comprising a sequence of SEQ ID NO: 25, a CDR2 region comprising a sequence of SEQ ID NO: 26 and a CDR3 region comprising a sequence of SEQ ID NO: 27; and a monoclonal antibody comprising a light chain comprising a CDR1 region comprising a sequence of SEQ ID NO: 28, a CDR2 region comprising a sequence of SEQ ID NO: 29 and a CDR3 region comprising a sequence of SEQ ID NO: 30, and a heavy chain comprising a CDR1 region comprising a sequence of SEQ ID NO: 31, a CDR2 region comprising a sequence of SEQ ID NO: 32 and a CDR3 region comprising a sequence of SEQ ID NO: 33.

In the present invention, the monoclonal antibody preferably comprises a light chain comprising a polynucleotide sequence of SEQ ID NO: 34, and a heavy chain comprising a polynucleotide sequence of SEQ ID NO: 35. The monoclonal antibody preferably has neutralizing activity against the influenza A virus H1 and H5 subtypes and has no neutralizing activity against the influenza A virus H3N2 subtype. The H1 subtype includes H1N1, H1N2, H1N3, H1N4, H1N5, H1N6, H1N7, H1N8 and H1N9, and the H5 subtype includes H5N1, H5N2, H5N3, H5N4, H5N5, H5N6, H5N7, H5N8 and H5N9.

In the present invention, the monoclonal antibody preferably comprises a light chain comprising a polynucleotide sequence of SEQ ID NO: 38, and a heavy chain comprising a polynucleotide sequence of SEQ ID NO: 39. The monoclonal antibody preferably has neutralizing activity against the influenza A virus H1, H2 and H5 subtypes and has no neutralizing activity against the influenza A virus H3N2 subtype. The H1 subtype includes H1N1, H1N2, H1N3, H1N4, H1N5, H1N6, H1N7, H1N8 and H1N9, and the H2 subtype includes H2N1, H2N2, H2N3, H2N4, H2N5, H2N6, H2N7, H2N8 and H2N9. Also, the H5 subtype includes H5N1, H5N2, H5N3, H5N4, H5N5, H5N6, H5N7, H5N8 and H5N9.

In the present invention, the monoclonal antibody preferably comprises a light chain comprising a polynucleotide sequence of SEQ ID NO: 42, and a heavy chain comprising a polynucleotide sequence of SEQ ID NO: 43. The monoclonal antibody preferably has neutralizing activity against the influenza A virus H1 subtype and has no neutralizing activity against the influenza A virus H3 subtype. The H1 subtype includes H1N1, H1N2, H1N3, H1N4, H1N5, H1N6, H1N7, H1N8 and H1N9.

The present invention also provides an isolated nucleic acid molecule encoding said anti-influenza A virus monoclonal antibody.

The nucleic acid molecule of the present invention includes all nucleic acid molecules obtained by "translating" the amino acid sequences of the antibodies of the present invention to polynucleotide sequences according to methods known to a person skilled in the art. Accordingly, various polynucleotide sequences with open reading frames (ORFs) can be prepared and are also included in the scope of the nucleic acid molecules of the present invention.

The present invention also provides an expression vector containing said nucleic acid molecule inserted therein. The expression vector can preferably be derived from one selected from the group consisting of, but not limited to, an MarEx expression vector produced by Celltrion Inc. (Korea), a commercially widely available pCDNA vector, F, R1, RP1, Col, pBR322, ToL, Ti vector; cosmids; phages such as lambda, lambdoid, M13, Mu, Pl, P22, Q[i, T-even, T2, T4, T7, etc; plant viruses. Any of a variety of expression vectors known to those skilled in the art can be used in the present invention, and the choice of the expression vector is dependent on the nature of the host cell of choice. Introduction of the vector in host cells can be effected by, but not limited to, calcium phosphate transfection, virus infection, DEAE-dextran mediated transfection, lipofectamin transfection or electroporation, and any person skilled in the art can select and use an introduction method suitable for the expression vector and host cell used. Preferably, the vector contains one or more selection markers, but is not limited thereto, and a vector containing no selection marker may also be used. The choice of the selection markers may depend on the host cells of choice, although this is not critical to the present invention as is well known to persons skilled in the art.

To facilitate the purification of the nucleic acid molecule of the present invention, a tag sequence may be inserted into the expression vector. Examples of the tag include, but are not limited to, a hexa-histidine tag, a hemagglutinin tag, a myc tag or a FLAG tag. Any of tags facilitating purification, known to those skilled in the art, may be used in the present invention.

The present invention also provides an anti-influenza A virus monoclonal antibody-producing cell line transformed with said expression vector.

In the present invention, the cells include, but are not limited to, the mammalian cell, the plant cell, the insect cell, the fungal cell or the bacterial origin cell. As for the mammalian cell, one selected from the group consisting of, but not limited to, CHO cell, F2N cell, CSO cell, BHK cell, Bowes melanoma cell, HeLa cell, 911 cell, AT1080 cell, A549 cell, HEK 293 cell and HEK293T cell, may preferably be used as a host cell. Any cell usable as mammalian host cell known to those skilled in the art may be used in the present invention.

The present invention also provides a method of screening an antibody having a neutralizing activity against influenza A virus in patients recovered from infection with influenza A virus, the method comprising the steps of: 1) examining whether patients infected with influenza A virus is completely recovered, and screening patients, who are negative for influenza A virus in blood, from the examined patients; 2) collecting blood from the completely recovered patients screened in step 1); 3) isolating B cells from the patient's blood collected in step 2); 4) screening B cells, which produce an HA-binding antibody, from the B cells isolated in step 3); 5) extracting RNAs from the B cells screened in step 4); 6) amplifying antibody genes from the RNAs extracted in step 5); 7) cloning the genes amplified in step 6) into expression vectors; 8) transfecting the expression vectors of step 7) into host cells; 9) examining whether the transfected host cells of step 8) produce the HA-binding antibody; 10) culturing the screened transfected cell of step 9); 11) purifying antibodies binding to the HA of influenza A virus from the transfected cell cultures of step 10); 12) re-confirming whether the antibodies purified in step 11) have neutralizing activity against influenza A virus; and 13) re-screening an antibody confirmed to have neutralizing activity against influenza A virus in step 12).

The present invention also provides a composition comprising said anti-influenza A virus monoclonal antibody.

The composition of the present invention may contain, in addition to the anti-influenza A virus monoclonal antibody, a pharmaceutically acceptable excipient. Pharmaceutically acceptable excipients are well known to those skilled in the art.

The present invention also provides a composition for preventing and treating a disease caused by influenza A virus, comprising said anti-influenza A virus monoclonal antibody.

The composition of the present invention may contain, in addition to the anti-influenza A virus monoclonal antibody, a pharmaceutically acceptable excipient. Pharmaceutically acceptable excipients are well known to those skilled in the art.

Also, the preventive and therapeutic composition of the present invention may comprise at least five other therapeutic agents for influenza A. The preventive and therapeutic composition of the present invention may comprise various monoclonal antibodies binding to the influenza A virus H1, H2 and H5 subtypes or fragments thereof, wherein the monoclonal antibodies can exhibit a synergistic effect on neutralizing activity. Also, the preventive and therapeutic composition of the present invention may additionally comprise one or more other therapeutic agents or diagnostic agents. The therapeutic agents include, but are not limited to, anti-viral drugs. Such drugs may include antibodies, small molecules, organic or inorganic compounds, enzymes, polynucleotide sequences, anti-viral peptides, etc.

The preventive and therapeutic composition of the present invention must be sterile and stable under the conditions of manufacture and storage. Also, it can be in powder form for reconstitution in the appropriate pharmaceutically acceptable excipient before or at the time of delivery. In the case of sterile powders for the preparation of sterile injectable solutions, the preferred methods of preparation are vacuum drying and freeze-drying that yield a powder of the active ingredient plus any additional desired ingredient from a previously sterile-filtered solution thereof. Alternatively, the composition of the present invention can be in solution and the appropriate pharmaceutically acceptable excipient can be added and/or mixed before or at the time of delivery to provide a unit dosage injectable form. Preferably, the pharmaceutically acceptable excipient used in the present invention is suitable to high drug concentration, can maintain proper fluidity and, if necessary, can delay absorption.

The choice of the optimal route of administration of the preventive and therapeutic composition will be influenced by several factors including the physico-chemical properties of the active molecules within the composition, the urgency of the clinical situation and the relationship of the plasma concentrations of the active molecules to the desired therapeutic effect. For example, the monoclonal antibodies of the present invention can be prepared with carriers that will protect them against rapid release, such as a controlled release formulation, including implants, transdermal patches, and microencapsulated delivery systems. Biodegradable, biocompatible polymers, such as ethylene vinyl acetate, polyanhydrides, polyglycolic acid, collagen, polyorthoesters, and polylactic acid, may be used in the present invention. Furthermore, the monoclonal antibody may be coated or co-administered with a material or compound that prevents the inactivation of the antibody. For example, the monoclonal antibody may be administered together with an appropriate carrier, for example, liposome or a diluent.

The routes of administration of the preventive and therapeutic composition of the present invention can be divided into oral and parenteral administration. The preferred administration route is intravenous, but is not limited thereto.

Oral dosage forms can be formulated as tablets, troches, lozenges, aqueous or oily suspensions, dispersible powders or granules, emulsions, hard capsules, soft gelatin capsules, syrups or elixirs, pills, dragees, liquids, gels, or slurries. These formulations can contain pharmaceutical excipients including, but not limited to, granulating and disintegrating agents, binding agents, lubricating agents, preservatives, coloring, flavoring or sweetening agents, vegetable or mineral oils, wetting agents, and thickening agents.

Formulations for parenteral administration can be in the form of aqueous or non-aqueous isotonic sterile non-toxic injection or infusion solutions or suspensions. The solutions or suspensions may comprise agents that are non-toxic to recipients at the dosages and concentrations employed such as 1,3-butanediol, Ringer's solution, Hank's solution, isotonic sodium chloride solution, oils, fatty acids, local anaesthetic agents, preservatives, buffers, viscosity or solubility increasing agents, water-soluble antioxidants, oil-soluble antioxidants and metal chelating agents.

The present invention provides a composition for diagnosis of influenza A virus, which comprises a conjugate comprising a tag conjugated to said anti-influenza A virus monoclonal antibody.

The diagnostic composition of the present invention comprises at least one detectable tag, such as a detectable moiety/agent. The tag can be conjugated non-covalently to the monoclonal antibody of the present invention. The tag can also be conjugated directly to the monoclonal antibody through covalent bonding. Alternatively, the tag can be conjugated to the monoclonal antibody by means of one or more linking compounds. Techniques for conjugating the tag to the monoclonal antibody are well known to those skilled in the art. The detectable moiety/agent as the tag is preferably one selected from the group consisting of, but not limited to, enzymes, prosthetic groups, fluorescent materials, luminescent materials, bioluminescent materials, radioactive materials, positron emitting metals, and non-radioactive paramagnetic metal ions.

The present invention also provides a method of treating a disease caused by influenza A virus, the method comprising a step of administering an influenza A virus monoclonal antibody of the present invention to a subject having a disease caused by influenza A virus.

In the therapeutic method of the present invention, the influenza A virus is preferably at least one selected from the group consisting of H1, H2 and H5 subtypes. The H1 subtype includes H1N1, H1N2, H1N3, H1N4, H1N5, H1N6, H1N7, H1N8 and H1N9, and the H2 subtype includes H2N1, H2N2, H2N3, H2N4, H2N5, H2N6, H2N7, H2N8 and H2N9. Also, the H5 subtype includes H5N1, H5N2, H5N3, H5N4, H5N5, H5N6, H5N7, H5N8 and H5N9.

In the therapeutic method of the present invention, any therapeutic agent for disease caused by influenza A virus known to those skilled in the art may be administered together with the monoclonal antibody of the present invention.

In the therapeutic method of the present invention, the disease caused by influenza A virus may be one selected from the group consisting of, but not limited to, a new strain offlu, pandemic flu and seasonal flu.

In the therapeutic method of the present invention, the dose of the influenza A virus monoclonal antibody may be adjusted to the optimum response. The dose is, for example, 0.01-200 mg/kg, preferably 0.1-150 mg/kg, and more preferably 1-100 mg/kg, but is not limited thereto. Several divided doses may be administered daily, or the dose may be proportionally reduced as indicated by the exigencies of an individual's situation. The composition of the present invention may be administered in a single serving or in multiple servings spaced throughout the day. The mode of administration is not limited in the present invention and can be decided by the attending physician.

In the therapeutic method of the present invention, the routes of administration of the influenza A virus monoclonal antibody can be divided into oral administration and parenteral administration. The preferred administration route is intravenous, but is not limited thereto.

The present invention also provides a method for preventing a disease caused by influenza A virus, the method comprising a step of administering an influenza A virus monoclonal antibody of the present invention to a subject.

In the preventive method of the present invention, the influenza A virus monoclonal antibody may be administered together with any preventive agent for disease caused by influenza A virus known to those skilled in the art.

In the preventive method of the present invention, the dose of the influenza A virus monoclonal antibody may be adjusted to the optimum response. The dose is, for example, 0.01-200 mg/kg, preferably 0.1-150 mg/kg, and more preferably 1-100 mg/kg, but is not limited thereto. Several divided doses may be administered daily, or the dose may be proportionally reduced as indicated by the exigencies of an individual's situation. The composition of the present invention may be administered in a single serving or in multiple servings spaced throughout the day. The mode of administration is not limited, and can be decided by the attending physician.

The present invention also provides a method for diagnosis of influenza A virus infection in a patient, the method comprising the steps of: 1) contacting a sample with the anti-influenza A virus monoclonal antibody of the present invention; and 2) detecting a reaction between the monoclonal antibody and the sample. Alternatively, the diagnostic method may comprise the steps of: 1) contacting a sample with a diagnostic composition of the present invention; and 2) detecting a reaction between the diagnostic composition and the sample.

In the diagnostic method of the present invention, the influenza A virus has one or more subtype(s) selected from the group consisting of H1, H2 and H5. The H1 subtype includes H1N1, H1N2, H1N3, H1N4, H1N5, H1N6, H1N7, H1N8 and H1N9, and the H2 subtype includes H2N1, H2N2, H2N3, H2N4, H2N5, H2N6, H2N7, H2N8 and H2N9. Also, the H5 subtype includes H5N1, H5N2, H5N3, H5N4, H5N5, H5N6, H5N7, H5N8 and H5N9.

In the diagnostic method of the present invention, the monoclonal antibody of the present invention may, if necessary, be conjugated with a tag for diagnosis and detection according to any method known to a person skilled in the art.

In the diagnostic method of the present invention, the sample is preferably one selected from the group consisting of, but not limited to, phlegm, spittle, blood, lung cell, lung tissue mucus, respiratory tissue and salvia. The sample can be prepared according to any conventional method known to a person skilled in the art.

In the diagnostic method of the present invention, the method for detecting the reaction may be one selected from the group consisting of, but not limited to, homogeneous and heterogeneous binding immunoassays, such as radio-immunoassays (RIA), ELISA, immunofluorescence, immunohistochemistry, FACS, BIACORE and Western blot analyses. Any detection method known to a person skilled in the art may be used in the present invention.

The present invention also provides a kit for diagnosis of influenza A virus, which comprises: 1) an anti-influenza A virus monoclonal antibody of the present invention; and 2) a container.

In addition, the present invention provides a kit for diagnosis of influenza A virus infection, which comprises: 1) a composition for diagnosis of influenza A virus infection according to the present invention; and 2) a container.

In the diagnostic kit of the present invention, the influenza A virus has preferably one or more subtype(s) selected from the group consisting of H1, H2 and H5. The H1 subtype includes HIN1, H1N2, H1N3, H1N4, H1N5, H1N6, H1N7, H1N8 and H1N9, and the H2 subtype includes H2N1, H2N2, H2N3, H2N4, H2N5, H2N6, H2N7, H2N8 and H2N9. Also, the H5 subtype includes H5N1, H5N2, H5N3, H5N4, H5N5, H5N6, H5N7, H5N8 and H5N9.

In the diagnostic kit of the present invention, a solid support is included in the container 2). The monoclonal antibody of the present invention can be attached to a solid support, and this solid support may be porous or nonporous, planar or non-planar.

EXAMPLES

Example 1: Isolation of PBMC from Blood from Patients Who Recovered from Flu A recovered patient group consisted of patient volunteers who were 2-4 weeks after confirmation of new flu infections. The volunteers were confirmed to have no influenza virus (H1N1) in their blood and had an antibody against the new influenza virus. This study was performed under the approval of the Institutional Review Board (IRB). This patients group had the following characteristics: (1) the patients were not vaccinated against seasonal flu; (2) the patients were negative for other infectious viruses, that is, HBsAg, and were negative for anti-HCV antibody and anti-HIV antibody; (3) the patients were negative (identified by RT-PCR) for the influenza virus H1N1 subtype in plasma; (4) the patients showed a titer of 1:160 or higher in serum in ELISA assays for the (monomeric) HA(H1N1) of the influenza A virus H1N1 subtype. About 100 ml of whole blood was collected from the volunteers, and peripheral blood mononuclear cells (PBMCs) were isolated from the collected blood using Lymphoprep™ (Axis-Shield, Norway, 1114545). The isolated PBMCs were washed three times with phosphate-buffered saline, suspended at $2\times10^7$ cells/me in KM banker II freezing medium (Cosmobio, Japan, KOJ-16092010), and stored in a liquid nitrogen tank.

Example 2: Primary Screening of Monoclonal Antibodies

B cells secreting antigen-specific antibodies were screened using the method described by Jin et al. (Tin A. et al., 2009. *Nat Med.* 15, 1088-1092). Briefly, the PBMCs were added to each well of the prepared microarray chip at a density of one cell/well. Antibodies secreted from the single cells were confirmed by the precoated anti-human IgG antibody. Whether the screened antibody-secreting cells secreted HA-binding antibodies was examined using the labeled HA antigen by an enzyme-linked immunospot assay (ELISPOT; Sedgwick J. D., 2005, *Methods Mol Bio. Vol.* 302, pp. 314). The complete sequences of the heavy-chain and light-chain genes of the antibodies from the individual antibody-secreting cells were obtained by a reverse transcription-polymerase chain reaction (RT-PCR). The obtained heavy-chain and light-chain DNAs were inserted into pcDNA 3.1(+) expression vectors (Invitrogen, USA, V790-20) to prepare expression vectors producing each of the heavy chain and light chain of the antibodies. The prepared expression vectors were co-transfected into CHO cells. After that, using the antibodies derived from the transfected CHO cells, 82 antibodies binding to HA were primarily selected through the HA-ELISA described in Example 3 below. Herein, all the antibodies showing a reaction with HA were primarily screened without serially diluting the antibody samples.

Example 3: Second Step Screening of Monoclonal Antibodies and their Production In order to secondarily screen monoclonal antibodies having high binding affinity for recombinant HA from the 82 primarily screened antibodies, HA-ELISA was performed using monomeric HA and trimeric HA. Recombinant monomeric HA (11055-VO8H) from influenza A virus (A/California/04/2009) was purchased from Sino Biological Inc. (China). The purchased monomeric HA consisted of an extra-cellular domain (met 1-gln529) of HA comprising 10 polyhistidine residues at the C-terminus and was derived from transfected human cells. Recombinant trimeric HA (FR-180) was provided by IRR (Influenza Reagent Resource, USA). The trimeric HA from H1N1 (A/California/04/2009) included a thrombin cleavage site at the C-terminus, a trimerizing domain (foldon) and six histidine residues and was produced using a baculovirus system.

The reactivity of the antibody with the HA antigen was measured by ELISA using the HA and the antibody. Specifically, first, 50 μl of each of monomeric HA or trimeric HA (250 ng/rne) was coated onto each well of a 96-well microtiter plate (Nunc, Denmark, 449824). The plate was blocked with phosphate-buffered saline (Teknova, USA, D5120) containing 1% bovine serum albumin (BSA), and then a 3-fold serially diluted antibody sample (starting concentration: 1 μg/ml) was added to each well of the plate. Next, the plate was incubated at room temperature for 1 hour and then treated with peroxidase-labeled goat anti-human gamma antibody (Zymed, USA, 62.8420). After incubation for 1 hour at room temperature, the plate was incubated with tetramethylbenzydine (TMB; Sigma-Aldrich, USA, T0440), and the incubation was stopped by adding 1 N HCl. The absorbance at 450/570 nm was measured using a plate reader (Spectramax plus 384, Molecular Device), and the antigen-antibody reactivity was graphically expressed using Graphpad prism program (GraphPad Software Inc. USA).

Figure 2:
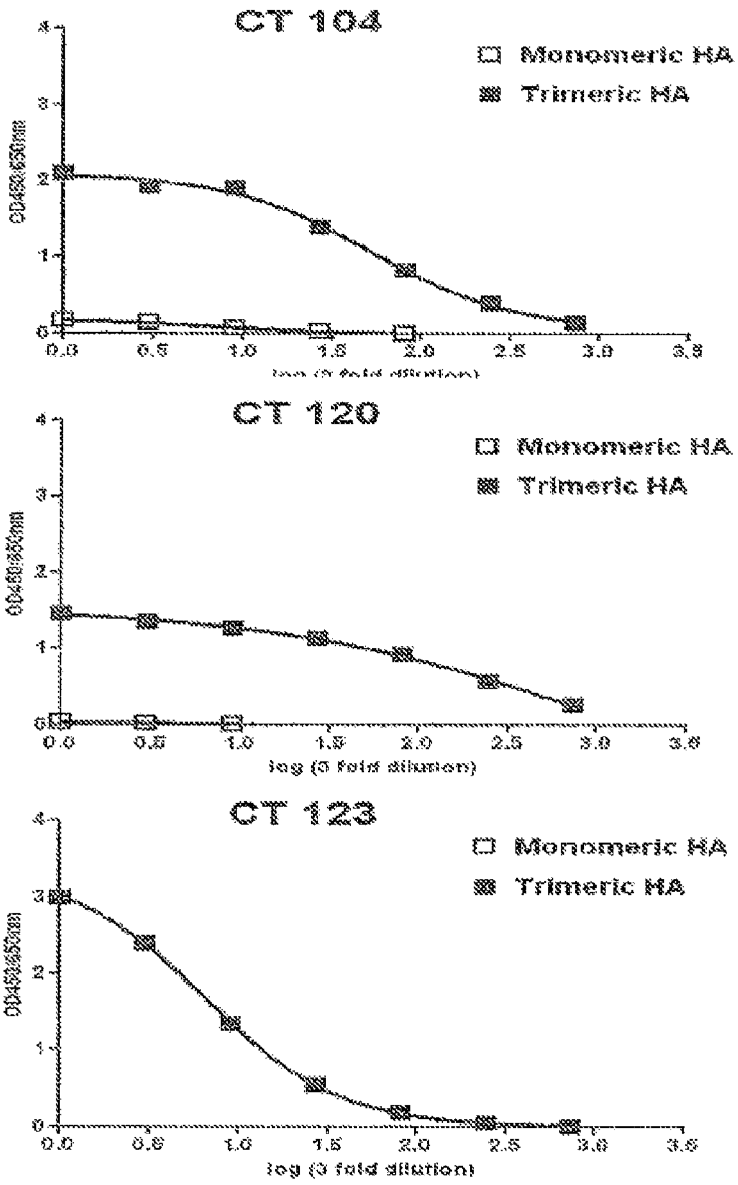
FIG. 2 is a set of graphs showing the binding affinities of CT104, CT120 and CT123 antibodies to monomeric HA and trimeric HA.

As shown in FIG. 1, the CT109, CT111-1 and CT154-2 antibodies showed very high binding activities against the trimeric HA and also showed high binding activities against the monomeric HA, but lower than the binding activities against the trimeric HA. Also, the CT104, CT120 and CT123 antibodies showed high binding activities against the trimeric HA, but showed little or no binding activities against the monomeric HA (FIG. 2). Other antibodies (CT137, CT151 and CT165 antibodies) showed little or no binding activities against the two antigens (FIG. 3).

Figure 3:
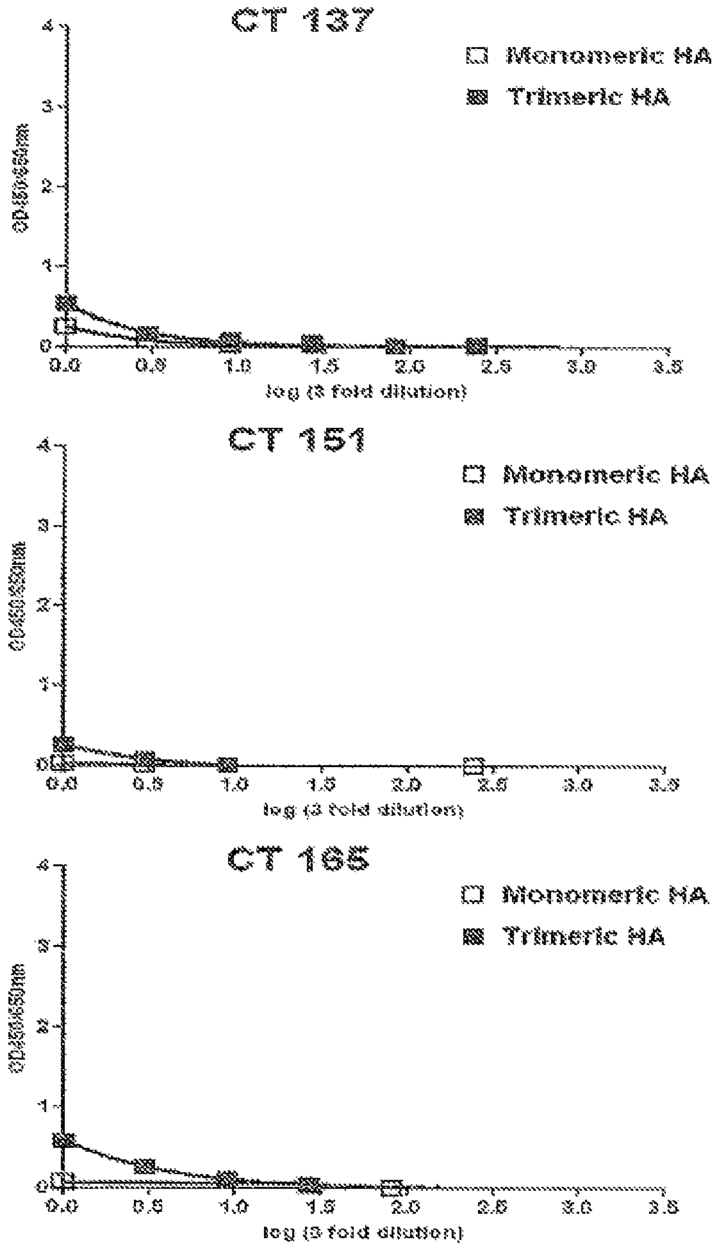
FIG. 3 is a set of graphs showing the binding affinities of CT137, CT151 and CT165 antibodies to monomeric HA and trimeric HA.

On the basis of the results shown in FIGS. 1 to 3, from the 82 primarily screened antibodies, 35 antibodies showing high binding activities against the trimeric HA were secondarily selected. To quantitate the binding activities of the monoclonal antibodies and thus narrow down the numbers of monoclonal antibodies in MN test, it was necessary to increase the expression levels of the secondarily selected antibodies. Therefore, these antibody genes were recloned from the cDNA vectors into MarEx expression vectors constructed and patented by Celltrion, Inc., in the following manner. After recloning, the MarEx expression vectors containing the antibody genes were used to produce antibodies required for a MN test and a HI test.

Figure 4A:
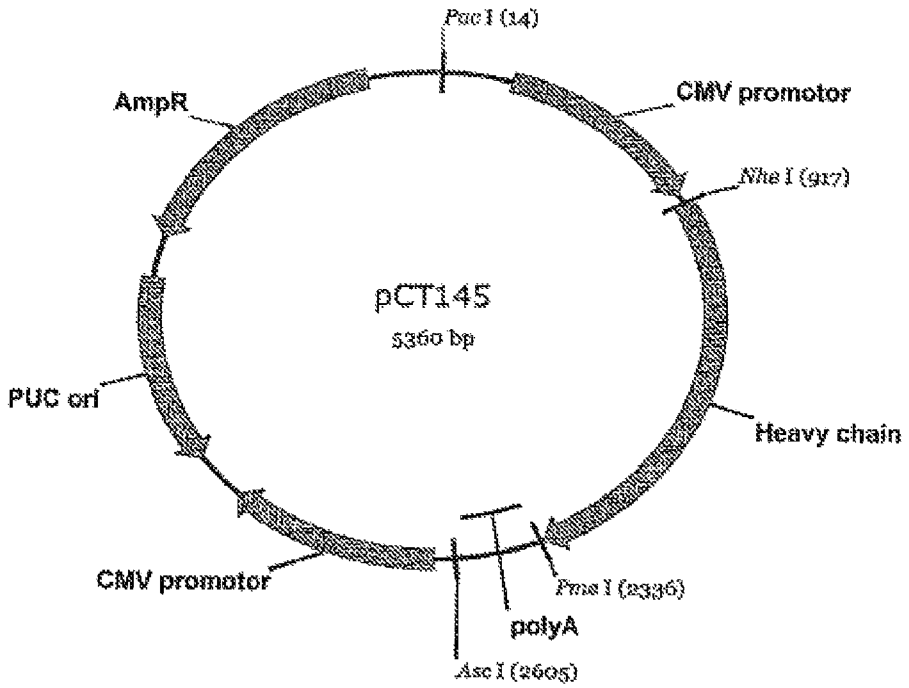
FIGS. 4A and 4B show vector maps of pCT145(A) and pCT147(B), in which A represents a pCT145 vector; B represents a pCT147 vector; pac: a gene which encodes a Puromycin N-acetyl-tranferase (PAC); and DS represents dyad symmetry (EBNA1 binds to the dyad symmetry (DS) element in oriP of EBV).
Figure 4B:
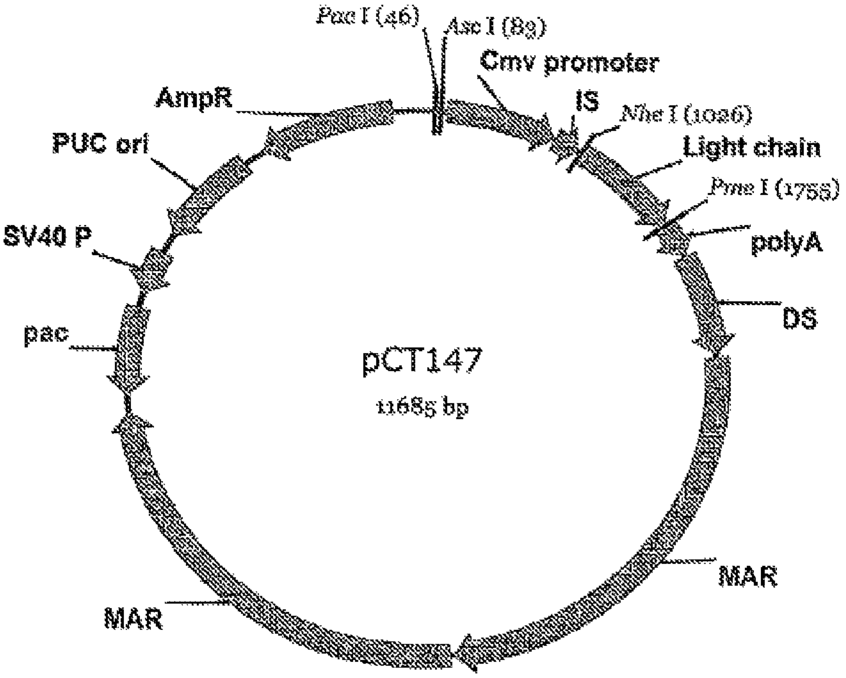
Figure 5:
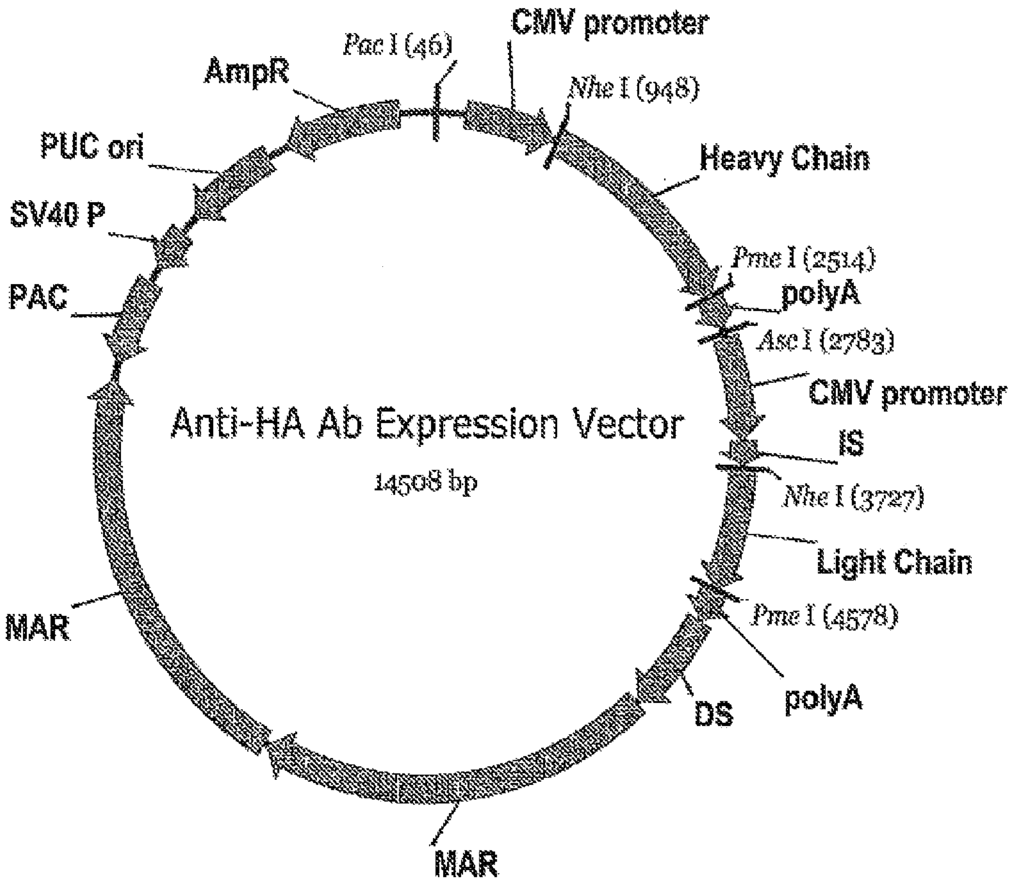
FIG. 5 is a map of an expression vector expressing the anti-influenza A virus monoclonal antibody of the present invention.

The original pcDNA vectors containing each of the heavy-chain genes and light-chain genes of the 35 secondarily selected antibodies were treated with the restriction enzymes Nhe I and Pme I to separate heavy-chain genes and light-chain genes. The obtained heavy-chain genes and light-chain genes were respectively inserted into pCT145 vectors and pCT147 vectors, which had been treated with the same restriction enzymes. The pCT145 and pCT147 vectors were constructed by Celltrion, Inc., in order to construct the heavy chain and the light chain expressing vectors, respectively (FIG. 4). Next, in order to construct expression vectors containing a heavy-chain transcription unit (promoter-heavy chain gene-poly A) together with a light-chain transcription unit (promoter-light chain gene-poly A), the pCT145 vectors containing the heavy-chain genes were treated with the restriction enzymes Pac I and Asc I to separate heavy-chain transcription units, and then the pCT147 vectors containing the light-chain genes were treated with the same restriction enzymes and inserted with the separated heavy-chain transcription units. Then, vectors containing the heavy-chain transcription unit together with the light-chain transcription unit were screened using restriction enzymes (FIG. 5). The screened vectors were extracted using an Endofree plasmid maxi kit (QIAGEN, Germany, 12362), and the nucleotide sequences were analyzed using the part of the extracted DNA samples, thereby determining the nucleotide sequences of the antibodies.

Next, the DNA of the extracted antibodies was transfected into suspension cell of F2N cell line (constructed by Celltrion, Inc., Korea), to produce monoclonal antibodies in transient production manner. Herein, the transfection was performed in the following manner. Transfection of the cells with plasmid DNA was carried out using the cationic polymer FreeStyle™ Max (Invitrogen, USA, 16447-100) according to the manufacturer's instruction. On the day before transfection, the F2N cells cultured in EX-CELL 293 serum-free media (SAFC, LIK, 14571C; hereinafter referred to as "EX-CELL 293 media") were centrifuged and suspended at a cell concentration of $1\times10^6$ cells/ml in modified EX-CELL 293 medium (SAFC, LIK, 65237; made to order), and 80 ml of the cell suspension was seeded into a 250 ml Erlenmeyer flask, or 200 ml of the cell suspension was seeded into a 1 1 Erlenmeyer flask in an amount of 200 ml. On the day of transfection, in the case in which 80 ml of the cell suspension was seeded, each of DNA encoding a monoclonal antibody and 100 μl of FreeStyle™ Max reagent was diluted to a volume of 1.6 ml using OptiPRO SFM II medium (Invitrogen, USA, 12309) and stirred gently. In the case in which 200 ml of the cell suspension was seeded, each of 250 μg of DNA and 250 μg of FreeStyle™ Max reagent was diluted to a volume of 4 ml using OptiPRO SFM II medium and stirred gently. Immediately after the stirring process, the solution containing FreeStyle™ Max reagent diluted therein was mixed with the solution containing DNA diluted therein, and the mixed solution was incubated at ambient temperature for 19 minutes. During the incubation process at ambient temperature for 19 minutes, the seeded F2N cells were diluted to a cell concentration of $0.8\times10^6$ cells using fresh modified EX-CELL 293 medium. After incubation for 19 minutes, the mixed solution of DNA and FreeStyle™Max reagent was added to the F2N cell culture prepared for transfection. On the day after transfection, the same amount of EX-CELL 293 medium was added to the transfected cells, which were then cultured for 7-8 days, thereby producing monoclonal antibodies.

Example 4: Examination of In Vitro Neutralizing Activity Against Viruses

From the screening of 35 monoclonal antibodies, 11 antibodies which showed high binding affinities to the trimeric HA in HA-ELISA were selected and subjected to a MN test in order to examine their neutralizing activity against various influenza viruses.

Example 4-1

Culture of MDCK Cell Line and Determination of Virus Concentration

As Madin-Darby canine kidney (MDCK) cell line, the London line (MDCK-L) was used. The MDCK cell line was cultured in a 5% $CO_2$ humidified incubator at 37° Cusing a DMEM medium (Gibco, USA, 11965) containing 10% FBS (Atlas Biologicals, USA, F0500A), 1× penicillin/streptomycin (Gibco, USA, 15140), 25 mM HEPES (Gibco, USA, 15630) and 2 mM L-glutamine (Gibco, USA, 25030).

Virus concentration was quantified by ELISA to determine the median tissue culture infective dose ($TCID_{50}$). The determination of virus concentration was performed in the following manner. First, a virus stock was serially diluted 10-fold with a virus diluent [DMEM (Gibco, USA), 3% BSA (Gibco, USA, 15260), 1× pecinillin/streptomycin (Gibco, USA), and 25 mM HEPES (Gibco, USA)], and 100 μl of the diluted virus was added to each well of a 96-well plate. As a negative control, a virus diluent containing no virus was used. Then, the MDCK cell line which was being cultured was treated with trypsin, separated from the culture incubator, and then treated with MDCK culture medium to neutralize trypsin. Next, the cell pellets were washed twice with phosphate-buffered saline, and then diluted to a cell concentration of $5\times10^5$ cells/ml with a virus diluent. 3-4 μg/ml of TPCK-trypsin (Sigma, USA) was added to the 96-well plate containing the virus, and then immediately, 100 μl of the MDCK cell line was added to each well of the plate and incubated in a 5% $CO_2$ humidified incubator at 37° C. for 20 hours. The incubated plate was washed once with phosphate buffered saline, and then 200 μl of a mixed solution of cold acetone: phosphate buffered saline (PBS) (80:20) was added to each well of the plate. Next, the cells were fixed for 8 minutes, and then the plate was dried at ambient temperature for 20 minutes. 200 μl of phosphate buffered saline was added to each well of the plate to wash each well twice. 100 μl of biotinylated anti-nuclear protein (NP) monoclonal antibody (Milipore, USA, MAB8257B), which was diluted 2,000-fold with 1% BSA-containing phosphate buffered saline, was added to each well of the plate and incubated at ambient temperature for 1 hour. The plate was washed three times with 200 μl/well of phosphate buffered saline, and a streptavidin-HRP-conjugated antibody was diluted 20,000-fold with 1% BSA-containing phosphate buffered saline. Then, 100 μl of the antibody dilution was added to each well of the plate and incubated at room pressure for 1 hour. After washing the plate four times with phosphate buffered saline, 100 μl of OPD solution (Sigma, USA, P8287) was added to each well, and the plate was developed at room temperature for 10 minutes. The plate was treated with 50 μl/well of 3 M HCl to stop the color development, and then the $OD_{490}$ of each well was measured. Based on the measured $OD_{490}$, $TCID_{so}$ was calculated using the method of Reed & Muench (The American 1938).

Example 4-2: MN Assay

Each antibody was diluted to a concentration of 10 μg/ml with a virus diluent. From this initial concentration, the antibody dilution was serially diluted 2-fold with a virus diluent, and 50 μl of the dilution was added to each well of a 96-well plate. Also, 50 j of viruses were added to each well of the plate at a concentration corresponding to 100 $TCID_{50}$ and were incubated in a 5% $CO_2$ humidified incubator at 37° C. for 1 hour. Next, 3-4 μg/ml of TPCK-trypsin (Sigma, USA, T1426) was added to each well, and 100 of the treated MDCK cells was added to each well, and then incubated in a 5% $CO_2$ humidified incubator at 37° C. for 20 hours. Then, an MN assay was carried out according to the same method as the virus quantification method described in Example 4-1, thus determining the $OD_{490}$ value of each well. The wells showing $OD_{490}$ values higher than that of the well introduced only with the cells was determined to be infected with viruses. Among $OD_{490}$ values for each antibody at which no virus antigen was detected, the lowest concentration (μg/ml) of the antibody is shown in Table 1, and the lower concentration of the antibody means the higher neutralizing activity against virus.

TABLE 1

Results of Micromeutralization assay (MN assay) carried out using screened antibodies and viruses of various types

| | H1 Pandemic | | H1 Seasonal | | H2 | H5 | | H3 |
|---|---|---|---|---|---|---|---|---|
| mab ID | (A/Texas/05/2009-RG15) | (A/New York/18/2009-RG18) | (A/Solomon Islands/2006) | (A/Ohio/83) | (A/Ann Arbor/ 6/60 ca) | (A/Viet-nam/1203/04) | (A/Anhui/1/05) | (A/Wiscon-sin/67/2005) |
| CT104 | 0.313 | 0.625 | 0.625 | 0.313 | >10 | 1.25 | 0.625 | >10 |
| CT105 | 1.25 | 5.0 | >10 | 2.5 | >10 | >10 | 10 | >10 |
| CT109 | >10 | >10 | >10 | >10 | >10 | >10 | >10 | >10 |
| CT111-1 | >10 | >10 | >10 | >10 | >10 | >10 | >10 | >10 |
| CT112-1 | 0.625 | 1.25 | 5.0 | 0.625 | >10 | 5 | 2.5 | >10 |
| CT113 | 1.25 | 1.25 | 1.25 | 0.625 | >10 | 5 | 2.5 | >10 |
| CT117 | 2.5 | 2.5 | 5.0 | 2.5 | >10 | 10 | 10 | >10 |
| CT119 | 1.25 | 2.5 | 5.0 | 1.25 | >10 | 10 | 2.5 | >10 |
| CT120 | 0.313 | 0.313 | 0.625 | 0.156 | 2.5 | 1.25 | 0.625 | >10 |
| CT122-1 | 2.5 | 10 | >10 | >10 | >10 | >10 | >10 | >10 |
| CT123 | 0.313 | 0.625 | 1.25 | 0.313 | >10 | >10 | >10 | >10 |

* unit: μg/ml

As can be seen from the results of MN assays of 11 candidate antibodies against H1, H2, H3 and H5 subtype influenza viruses, the CT104 showed neutralizing activities against two pandemic H1N1 subtype viruses (A/Texas/05/2009 and A/New York/18/2009) and two seasonal H1N1 subtype viruses (A/Solomon Islands/3/2006 and A/Ohio/83) at low concentrations (0.313-0.625 μg/ml) and also neutralized two H5N1 subtype viruses (A/Vietnam/1203/04 and A/Anhui/1/05) at concentrations of 1.25 μg/ml and 0.625 μg/ml, respectively. However, the CT104 antibody did not show neutralizing activity against the H2N2 subtype virus (A/Ann Arbor/6/60ca) and the H3N2 subtype virus (A/Wisconsin/67/2005). The CT123 showed neutralizing activity only against four H1N1 subtype viruses tested. Particularly, the CT120 antibody showed high neutralizing activity against the four H1N1 subtype influenza viruses, one H2N2 influenza subtype (A/Ann Arbor/6/60 ca) and two H5N1 subtype influenza viruses. However, the above-described antibodies did not show neutralizing activity against the H3N2 subtype belonging to the H3 Glade.

The $IC_{50}$ values of the three screened antibodies having neutralizing activity against viruses were measured for comparison, and the measurement results are shown in Table 2 below. Herein, the $IC_{50}$ value is the antibody concentration at which the antibody shows 50% of the highest neutralizing activity against viruses, and the lower value of $IC_{50}$ means the higher neutralizing activity of the antibody.

TABLE 2

IC50 values of neutralizing activities of CT104, CT120 and CT123 against two types of pandemic H1N1 viruses

| Antibody | A/Texas/05/2009-RG15 Antibody concentration* | A/Texas/05/2009-RG15 $IC_{50}$ | A/New Yock/18/2009-RG18 Antibody concentration* | A/New Yock/18/2009-RG18 $IC_{50}$ |
|---|---|---|---|---|
| CT104 | 0.313 μg/ml | 0.29 μg/ml | 1.25 μg/ml | 0.56 μg/ml |
| CT120 | 0.156 μg/ml | 0.15 μg/ml | 0.313 μg/ml | 0.31 μg/ml |
| CT123 | 0.625 μg/ml | 0.068 μg/ml | 1.25 μg/ml | 0.29 μg/ml |

Note.
Antibody concentration* is a neutralizing antibody concentrations shown in Table 1.

As can be seen in Table 2 above, the three antibodies had very low $IC_{50}$ values, and thus had high neutralizing activity against the two viruses shown in Table 2.

Example 5: Examination of the Ability of Antibody to Inhibit a Hemagglutination Reaction Caused by Viruses An antibody was serially diluted 2-fold on a V-bottom 96-well plate, and viruses of 4-fold HA unit were added to and mixed with the antibody. Next, the plate was incubated at room temperature for 30 minutes, and then 1% avian red blood cells were added to each well of the plate. The hemagglutination inhibition end point was determined as the lowest antibody concentration in which no hemagglutination-reaction was observed.

As a result, all the antibodies tested did not inhibit hemagglutination for two types of pandemic H1N1 subtype viruses (A/Texas/05/2009-RG15 and A/New York/18/2009-RG18) even at high concentrations (>20 μg/ml) (Table 3).

TABLE 3

Results of Hemagglutination-inhibition test for screened antibodies against two types of pandemic H1N1 viruses

| Antibody | A/Texas/05/2009-RG15 | A/New Yock/18/2009-RG18 |
|---|---|---|
| CT104 | >20 μg/ml | >20 μg/ml |
| CT105 | >20 μg/ml | >20 μg/ml |
| CT109 | >20 μg/ml | >20 μg/ml |
| CT111-1 | >20 μg/ml | >20 μg/ml |
| CT112-1 | >20 μg/ml | >20 μg/ml |
| CT113 | >20 μg/ml | >20 μg/ml |
| CT119 | >20 μg/ml | >20 μg/ml |
| CT120 | >20 μg/ml | >20 μg/ml |
| CT122-1 | >20 μg/ml | >20 μg/ml |
| CT123 | >20 μg/ml | >20 μg/ml |

Example 6: Examination of Preventive and Therapeutic Effects of Antibodies on Influenza Viruses Infection by Animal Experiment

Example 6-1: Mouse Survival Experiment

In order to examine the CT104, CT120 and CT123 antibodies screened in the above Examples have preventive and therapeutic effects against H1N1 and H5N1 subtype viruses in mice, the following experiment was carried out.

Figure 6A:
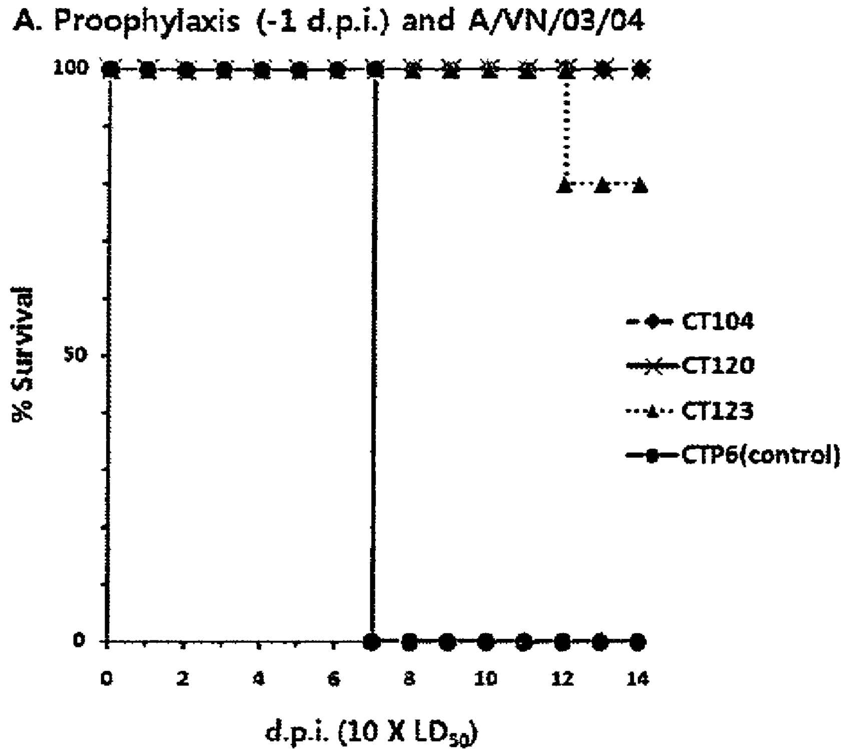
FIGS. 6A to 6D show the results of animal (mouse) survival experiments conducted using the anti-influenza A virus monoclonal antibody of the present invention, in which A represents a group injected with the antibodies 24 hours before challenging with H5N1 subtype virus (A/Vietnam/1203/04); B represents a group injected with the antibody 48 hours after challenging with H5N1 subtype virus (A/Vietnam/1203/04); C represents a group injected with the antibody 24 hours before challening with pandemic H1N1 subtype virus (A/California/07/2009); and D represents a group injected with the antibody 24 hours before challenging with seasonal H1N1 subtype virus (A/puertoRico/8/1934).
Figure 6B:
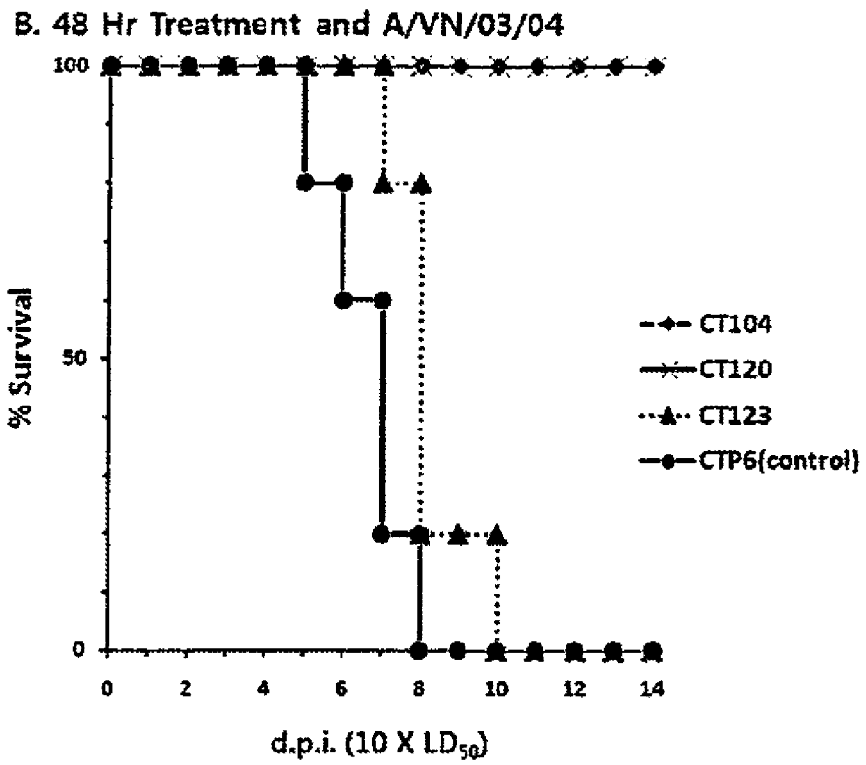

Each group consisting of five mice that were nasally infected with $10\times LD_{50}$ of viruses. Each of the three screened antibodies (CT-104, CT-120 and CT123) and a negative control antibody (CT-P6) was administered to mice by intra-abdominal injection in an amount of 10 mg/kg of mice 24 hours before virus infection and 48 hours after virus infection. The experimental results are shown in FIG. 6. As shown in FIG. 6, when the CT-104 or the CT-120 was injected into mice 24 hours before infection with $10\times LD_{50}$ of H5N1 subtype virus (A/Vietnam/1203/2004), all the mice survived, but when mice were treated with the CT-123, 20% of the mice died after 12 days. In the case of the negative control antibody (CT-P6), the mice injected with the control antibody all died after 7 days (FIG. 6A). When the antibodies were injected 2 days after virus infection in order to examine the therapeutic effects of the antibodies, the mice injected with the CT-104 and the CT-120 all survived up to day 14, the last day of the observation period, but the mice injected with the negative control antibody (CT-P6) or the CT-123 all died (FIG. 6B).

Figure 6C:
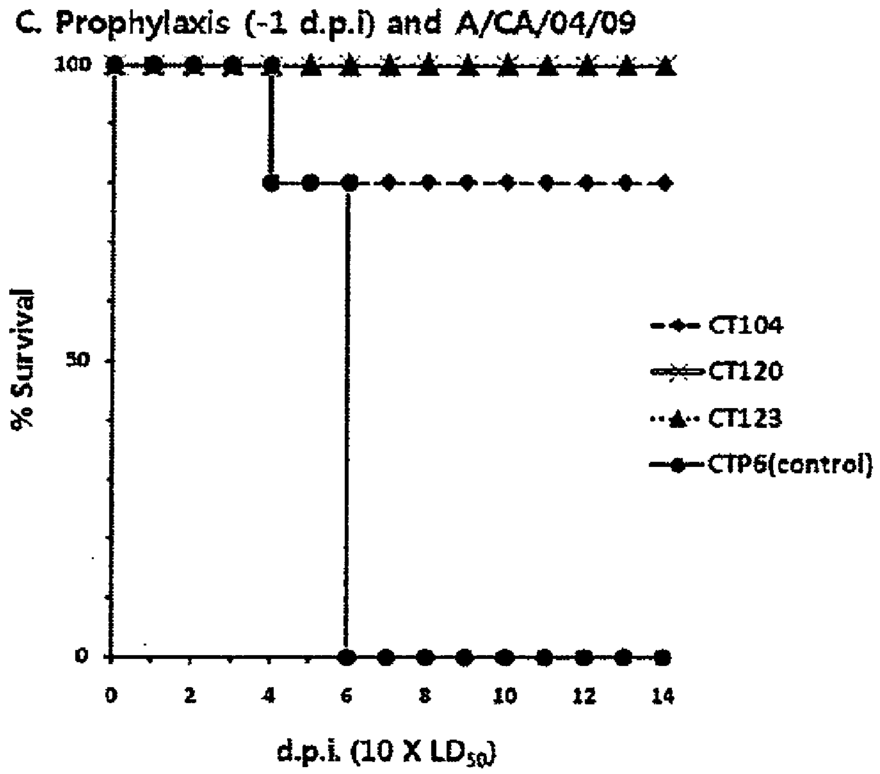

When the antibodies were injected 24 hours before infection with the pandemic H1N1 subtype virus (A/California/07/2009) in order to examine the preventive effects of the antibodies, the mice injected with the CT-120 and the CT-123 all survived up to day 14, the last day of the observation period, and 80% of the mice injected with the CT-104 survived, but the mice injected with the negative control antibody (CT-P6) all died (FIG. 6C).

Figure 6D:
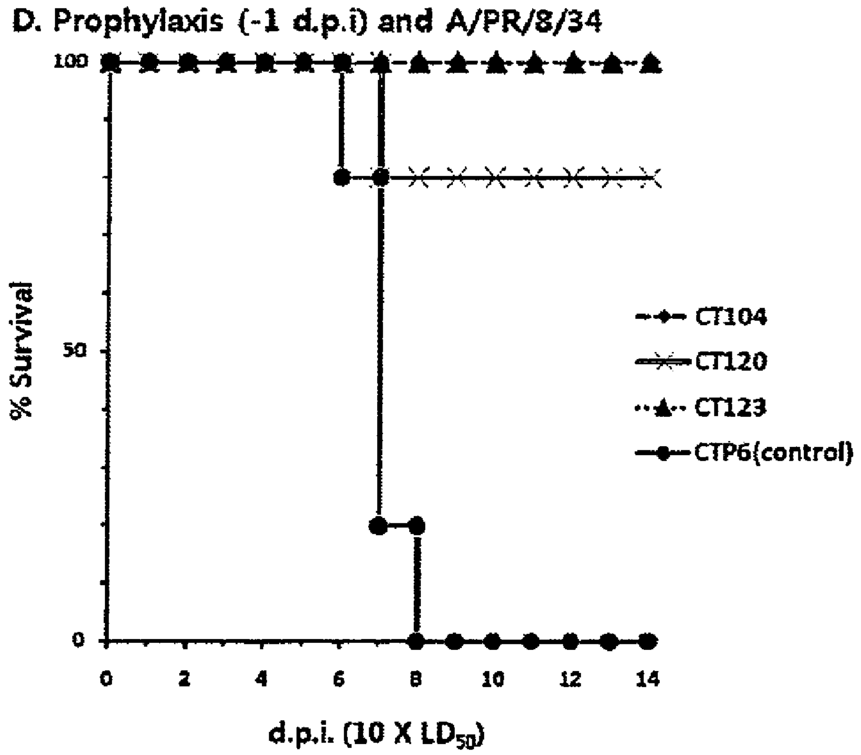

In addition, the mice administered with the CT-104 or the CT-123 24 hours before infection with the seasonal H1N1 subtype virus (A/Puerto Rico/8/1934) all mice survived for the observation period, and the mice administered with the CT-120 showed a survival rate of 80%, but the mice injected with the negative control antibody (CT-P6 antibody) all died (FIG. 6D).

Example 6-2: Ferret Experiment

To investigate the curative virtues, the selected CT120 was tested on ferret animal model, which shows similar sensitivities and symptoms to that of human against influenza virus.

Each test group was composed of 9 ferrets except negative control group including additional 4 ferrets to measure the initial concentration of viral infection. Ferrets were intranasally or intratracheally inoculated with 1 ml ($1\times10^6$ $EID_{50}$/ml) of the influenza virus [A/California/04/09 (H1N1)] after acclimatization. CT120 was intravenously injected once at 24 hr after viral inoculation: test group 1 was injected with 15 mg/kg of CT120; test group 2 was injected with 30 mg/kg of CT120. For test group 3, 30 mg/kg of CT120 was injected every 24 hr for 3 days. For negative control group, 30 mg/kg of CT-P6 antibody was intravenously injected once at 24 hr after viral inoculation.

Each nasal wash was collected from ferrets of each test group at 1, 3, 5, and 8 days after viral inoculation and the viral concentrations in collected samples were measured using fertile eggs. 3 ferrets of each test group were sacrificed at 1, 3, 5, and 8 days after viral inoculation and the viral concentrations in removed lung tissues were measured using fertile eggs.

Each lung tissue was ground using homogenizer in PBS including antibiotics (1 ml for each 1 g of lung tissues) and then supernatant was removed following centrifugation.

Each nasal wash was collected with 1 ml of PBS including antibiotics and then supernatant was removed following centrifugation to measure the viral concentration. Supernatants of either lung tissue homogenate or nasal wash was ten-fold serially diluted with PBS including antibiotics and then 10-13 day old fertile eggs were inoculated with the diluted supernatant. The mixtures of allantoic fluid (50 μl) from 48 hours-incubated fertile eggs and the same volume of 0.5% red blood cells (turkey) were incubated for 30 minutes and then virus was titrated by agglutination of blood.

Figure 7:
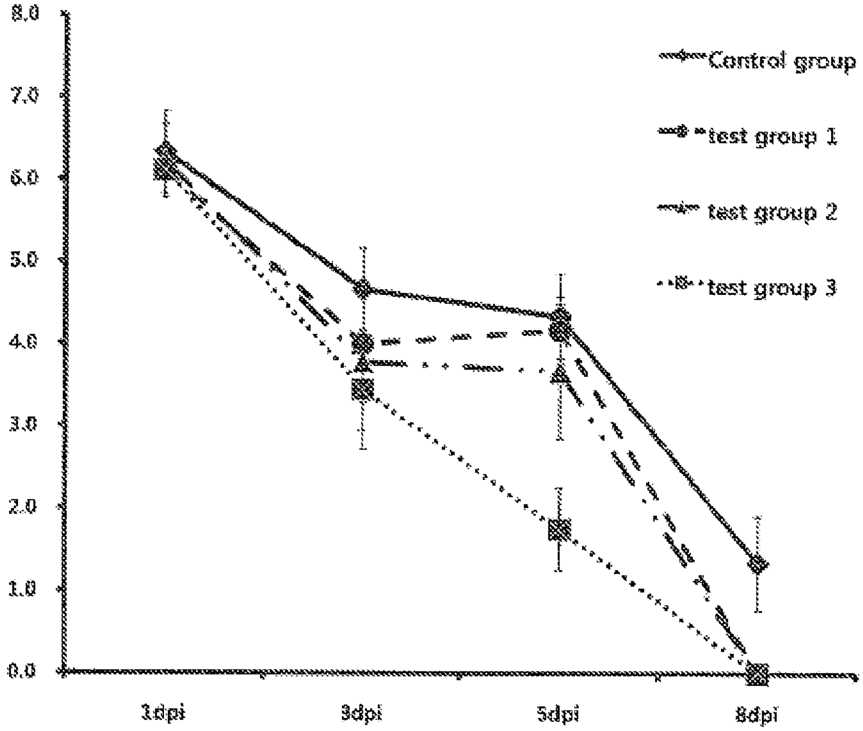
FIG. 7 shows results of the virus titer-change in nasal wash of animal (ferret) experiments conducted using the CT120 of the present invention 24 hours after challenging with H1N1 subtype (A/California/04/09).

Although viral titer in nasal wash remained high (>log 10 4 $EID_0$/ml) until 5 day post inoculation and then decreased in control group, viral titer was significantly decreased in CT120-injected group and no virus was detected at 8 day post-inoculation (FIG. 7). Thus, more rapid viral clearance was observed in CT120-treated group than in control group. Especially, virus was more significantly suppressed when the antibody was injected daily for the initial 3 days in test group 3.

Figure 8:
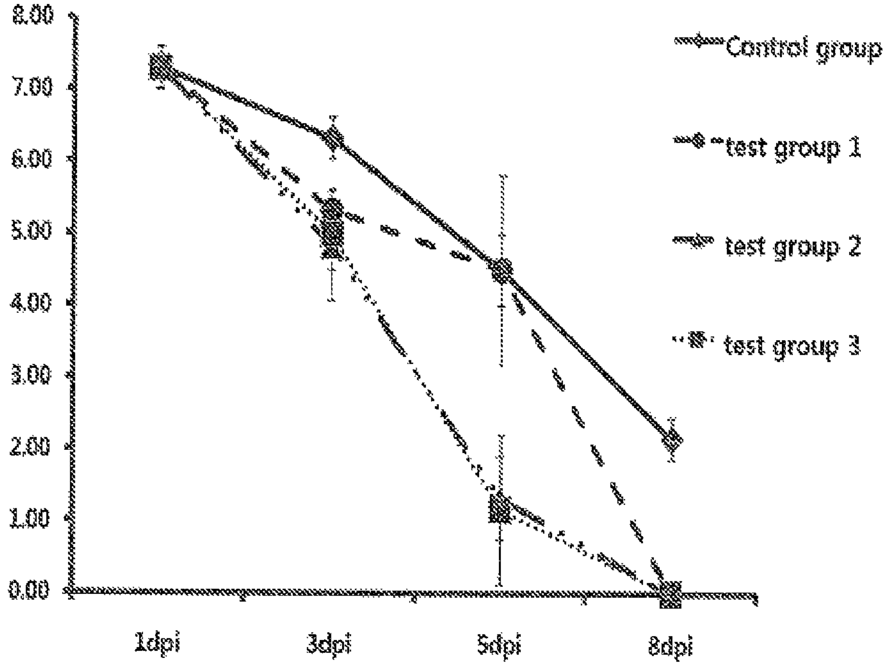
FIG. 8 shows results of the virus titer-change in lung tissue of animal (ferret) experiments conducted using the CT120 of the present invention after challenging with H1N1 subtype (A/California/04/09).

Viral titer in lung tissues remained high (>log 4.5 $EID_{50}$/me) until 5 day post challenge and then decreased in control group, whereas viral titer was markedly decreased in CT120-injected group. No virus was detected at 8 day post-challenge (FIG. 8). Especially, ferret experiment showed that virus is more significantly suppressed in test group 2 and 3. These results demonstrate that 30 mg/kg of CT120 more effectively suppress viral proliferation than 15 mg/kg dosage.

The invention claimed is:

1. An anti-influenza A virus monoclonal antibody selected from the group consisting of the following monoclonal antibodies:

(a) a monoclonal antibody comprising a light chain comprising a CDR1 region comprising a sequence of SEQ ID NO: 1, a CDR2 region comprising a sequence of SEQ ID NO: 2 and a CDR3 region comprising a sequence of SEQ ID NO: 3, and a heavy chain comprising a CDR1 region comprising a sequence of SEQ ID NO: 4, a CDR2 region comprising a sequence of SEQ ID NO: 5 and a CDR3 region comprising a sequence of SEQ ID NO: 6;

(b) a monoclonal antibody comprising a light chain comprising a CDR1 region comprising a sequence of SEQ ID NO: 7, a CDR2 region comprising a sequence of SEQ ID NO: 2 and a CDR3 region comprising a sequence of SEQ ID NO: 8, and a heavy chain comprising a CDR1 region comprising a sequence of SEQ ID NO: 9, a CDR2 region comprising a sequence of SEQ ID NO: 10 and a CDR3 region comprising a sequence of SEQ ID NO: 11; and (c) a monoclonal antibody comprising a light chain comprising a CDR1 region comprising a sequence of SEQ ID NO: 12, a CDR2 region comprising a sequence of SEQ ID NO: 2 and a CDR3 region comprising a sequence of SEQ ID NO: 13, and a heavy chain comprising a CDR1 region comprising a sequence of SEQ ID NO: 14, a CDR2 region comprising a sequence of SEQ ID NO: 15 and a CDR3 region comprising a sequence of SEQ ID NO: 16, wherein the monoclonal antibody is produced by a non-human mammalian cell culture.

2. The anti-influenza A virus monoclonal antibody of claim 1, wherein the monoclonal antibody comprises a light chain comprising a polypeptide sequence of SEQ ID NO: 36, and a heavy chain comprising a polypeptide sequence of SEQ ID NO: 37.

3. The anti-influenza A virus monoclonal antibody of claim 1, wherein the monoclonal antibody comprises a light chain comprising a sequence of SEQ ID NO: 40, and a heavy chain comprising a sequence of SEQ ID NO: 41.

4. The anti-influenza A virus monoclonal antibody of claim 1, wherein the monoclonal antibody comprises a light chain comprising a polypeptide sequence of SEQ ID NO: 44, and a heavy chain comprising a polypeptide sequence of SEQ ID NO: 45.

5. The anti-influenza A virus monoclonal antibody of claim 1, wherein the non-human mammalian cell culture is CHO cells, COS cells or BHK cells.

6. An anti-influenza A virus monoclonal antibody selected from the group consisting of the following monoclonal antibodies:

(a) a monoclonal antibody comprising a light chain comprising a CDR1 region comprising a polypeptide encoded by a polynucleotide sequence set forth in SEQ ID NO: 17, a CDR2 region comprising a polypeptide encoded by a polynucleotide sequence set forth in SEQ ID NO: 18 and a CDR3 region comprising a polypeptide encoded by a polynucleotide sequence set forth in SEQ ID NO: 19, and a heavy chain comprising a CDR1 region comprising a polypeptide encoded by a polynucleotide sequence set forth in SEQ ID NO: 20, a CDR2 region comprising a polypeptide encoded by a polynucleotide sequence set forth in SEQ ID NO: 21 and a CDR3 region comprising a polypeptide encoded by a polynucleotide sequence set forth in SEQ ID NO: 22;

(b) a monoclonal antibody comprising a light chain comprising a CDR1 region comprising a polypeptide encoded by a polynucleotide sequence set forth in SEQ ID NO: 23, a CDR2 region comprising a polypeptide encoded by a polynucleotide sequence set forth in SEQ ID NO: 18 and a CDR3 region comprising a polypeptide encoded by a polynucleotide sequence set forth in SEQ ID NO: 24, and a heavy chain comprising a CDR1 region comprising a polypeptide encoded by a polynucleotide sequence set forth in SEQ ID NO: 25, a CDR2 region comprising a polypeptide encoded by a polynucleotide sequence set forth in SEQ ID NO: 26 and a CDR3 region comprising a polypeptide encoded by a polynucleotide sequence set forth in SEQ ID NO: 27; or (c) a monoclonal antibody comprising a light chain comprising a CDR1 region comprising a polypeptide encoded by a polynucleotide sequence set forth in SEQ ID NO: 28, a CDR2 region comprising a polypeptide encoded by a polynucleotide sequence set forth in SEQ ID NO: 29 and a CDR3 region comprising a polypeptide encoded by a polynucleotide sequence set forth in SEQ ID NO: 30, and a heavy chain comprising a CDR1 region comprising a polypeptide encoded by a polynucleotide sequence set forth in SEQ ID NO: 31, a CDR2 region comprising a polypeptide encoded by a polynucleotide sequence set forth in SEQ ID NO: 32 and a CDR3 region comprising a polypeptide encoded by a polynucleotide sequence set forth in SEQ ID NO: 33.

7. The anti-influenza A virus monoclonal antibody of claim 6, wherein the binding molecule comprises a light chain comprising a polypeptide sequence of SEQ ID NO: 34, and a heavy chain comprising a polypeptide sequence of SEQ ID NO: 35.

8. The anti-influenza A virus monoclonal antibody of claim 6, wherein the binding molecule comprises a light chain comprising a sequence of SEQ ID NO: 38, and a heavy chain comprising a sequence of SEQ ID NO: 39.

9. The anti-influenza A virus monoclonal antibody of claim 6, wherein the binding molecule comprises a light chain comprising a polypeptide sequence of SEQ ID NO: 42, and a heavy chain comprising a polypeptide sequence of SEQ ID NO: 43.

10. The anti-influenza A virus monoclonal antibody of claim 6, wherein the monoclonal antibody is produced by a non-human mammalian cell culture.

11. The anti-influenza A virus monoclonal antibody of claim 10, wherein the non-human mammalian cell culture is CHO cells, COS cells or BHK cells.

12. A composition comprising the anti-influenza A virus monoclonal antibody of claim 1.

13. A composition for preventing and treating a disease caused by influenza A virus, the composition comprising the anti-influenza A virus monoclonal antibody of claim 1.

14. A composition for diagnosis of influenza A virus, the composition comprising a conjugate comprising a tag linked to the anti-influenza A virus monoclonal antibody of claim 1.

15. The composition of claim 14, wherein the tag is any one selected from the group consisting of enzymes, luciferases, radioactive isotopes, and toxin.

16. A kit for diagnosis of influenza A virus, comprising:

i) the anti-influenza A virus monoclonal antibody of claim 1; and ii) a container.

17. The kit of claim 16, wherein the influenza A virus is selected from the group consisting of H 1, H2, and H5 subtypes.

18. A composition comprising the anti-influenza A virus monoclonal antibody of claim 6.

19. A composition for preventing and treating a disease caused by influenza A virus, the composition comprising the anti-influenza A virus monoclonal antibody of claim 6.

20. A composition for diagnosis of influenza A virus, the composition comprising a conjugate comprising a tag linked to the anti-influenza A virus monoclonal antibody of claim 6.

21. The composition of claim 20, wherein the tag is any one selected from the group consisting of enzymes, luciferases, radioactive isotopes, and toxin.

22. A kit for diagnosis of influenza A virus, comprising:

i) the anti-influenza A virus monoclonal antibody of claim 6; and ii) a container.

23. The kit of claim 22, wherein the influenza A virus is selected from the group consisting of H 1, H2, and H5 subtypes.

* * * * *